(12) United States Patent
Higuchi et al.

(10) Patent No.: US 8,518,441 B2
(45) Date of Patent: Aug. 27, 2013

(54) SOLID DISPERSIONS OR SOLID DISPERSION PHARMACEUTICAL PREPARATIONS OF PHENYLALANINE DERIVATIVES

(75) Inventors: Hiroyuki Higuchi, Kawasaki (JP); Hirokazu Hagio, Kawasaki (JP); Kenichi Ogawa, Kawasaki (JP); Akira Yabuki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 143 days.

(21) Appl. No.: 11/433,589

(22) Filed: May 15, 2006

(65) Prior Publication Data
US 2006/0204572 A1 Sep. 14, 2006

Related U.S. Application Data

(63) Continuation of application No. PCT/JP2004/016942, filed on Nov. 15, 2004.

(30) Foreign Application Priority Data

Nov. 14, 2003 (JP) ................................. 2003-385501

(51) Int. Cl.
  A61K 9/22 (2006.01)
  A61K 31/517 (2006.01)
  A61K 9/20 (2006.01)
(52) U.S. Cl.
  USPC ......... 424/464; 424/455; 424/468; 514/266.3
(58) Field of Classification Search
  None
  See application file for complete search history.

(56) References Cited

U.S. PATENT DOCUMENTS

| | | | | |
|---|---|---|---|---|
| 4,654,206 | A * | 3/1987 | Okuda et al. | 424/480 |
| 6,107,276 | A * | 8/2000 | Carli et al. | 514/11 |
| 6,329,372 | B1 * | 12/2001 | Head et al. | 514/241 |
| 6,462,093 | B1 | 10/2002 | Miyamoto et al. | |
| 7,399,485 | B1 | 7/2008 | Shimizu et al. | |
| 2001/0031788 | A1 | 10/2001 | Schoop et al. | |
| 2003/0220268 | A1 | 11/2003 | Makino et al. | |
| 2003/0220318 | A1 | 11/2003 | Suzuki et al. | |
| 2005/0222141 | A1 | 10/2005 | Sagi et al. | |
| 2006/0009476 | A1 | 1/2006 | Kataoka et al. | |
| 2007/0014856 | A1 | 1/2007 | Takagi et al. | |

FOREIGN PATENT DOCUMENTS

| | | |
|---|---|---|
| EP | 0 988 863 A2 | 3/2000 |
| EP | 0 988 863 A3 | 3/2000 |
| EP | 1 288 205 A1 | 3/2003 |
| JP | 60-38322 | 2/1985 |
| JP | 05-004919 A | 1/1993 |
| JP | 05-310571 A | 11/1993 |
| JP | 07-324086 | 12/1995 |
| JP | 11-246404 | 9/1999 |
| JP | 2000-103731 A | 4/2000 |
| JP | 2000-191518 A | 7/2000 |
| JP | 2000-281561 | 10/2000 |
| JP | 2001-163769 A | 6/2001 |

(Continued)

OTHER PUBLICATIONS

Dianzhou BI, et al., Pharmaceutics 4th edition, People's Medical Publishing House, 1999, 8 pages (with English translation).
K. Okimoto, et al., "Dissolution Mechanism and Rate of Solid Dispersion Particles of Nilvadipine with Hydroxypropylmethylcellulose", International Journal of Pharmaceutics, 159, 1997, pp. 85-93.

(Continued)

*Primary Examiner* — Daniel Sullivan
*Assistant Examiner* — Kyle Purdy
(74) *Attorney, Agent, or Firm* — Oblon, Spivak, McClelland, Maier & Neustadt, L.L.P.

(57) ABSTRACT

The present invention provides solid dispersions or solid dispersion pharmaceutical preparations containing a water-soluble polymeric substance(s) and a phenylalanine compound of the formula (1) or pharmaceutically acceptable salts thereof, wherein A represents the formula (2) and the like, B represent an alkoxy group and the like, E represents a hydrogen atom and the like, D represents a substituted phenyl group and the like, T, U and V represent a carbonyl group and the like, Arm represents a benzene ring and the like, R1 represents an alkyl group and the like, R2, R3, and R4 may be the same or different from one another and each represent a hydrogen atom, a substituted amino group and the like, and J and J' represent a hydrogen atom and the like; production methods thereof; and solubilized pharmaceutical preparations containing a solubilizer(s) and the compound (I) or pharmaceutically acceptable salts thereof. According to the solid dispersion pharmaceutical preparations or solubilized pharmaceutical preparations, though they contain the phenylalanine compound of the formula (1) that is a poorly-soluble drug as an active ingredient, the pharmaceutical preparations having high solubility and oral absorbability can be obtained.

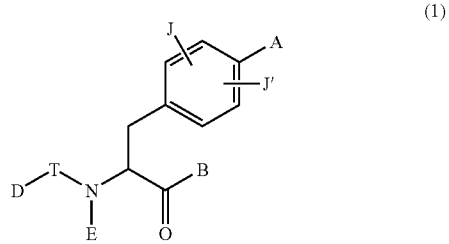

(1)

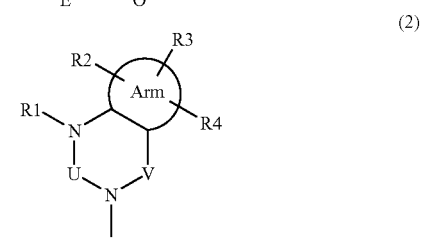

(2)

13 Claims, 5 Drawing Sheets

(56) References Cited

FOREIGN PATENT DOCUMENTS

| | | |
|---|---|---|
| JP | 2001-335483 | 12/2001 |
| JP | 2003-238507 | 8/2003 |
| JP | 3440469 B2 | 8/2003 |
| WO | WO 95/32713 | 12/1995 |
| WO | WO 96/19239 A1 | 6/1996 |
| WO | WO 98/27137 | 7/1998 |
| WO | WO 99/06437 | 2/1999 |
| WO | WO 99/22738 A1 | 5/1999 |
| WO | WO 00/29025 | 5/2000 |
| WO | WO 00/31118 | 6/2000 |
| WO | WO 01/78716 A1 | 10/2001 |
| WO | WO 02/16329 | 2/2002 |
| WO | WO 02/069932 A1 | 9/2002 |
| WO | WO 03/024426 A1 | 3/2003 |
| WO | WO 03/68728 | 8/2003 |
| WO | WO 2004/074264 | 9/2004 |
| WO | WO 2005/046697 | 5/2005 |
| WO | WO 2005/051925 | 6/2005 |

OTHER PUBLICATIONS

F. Cilurzo, et al., "Characterization of Nifedipine Solid Dispersions", International Journal of Pharmaceutics, 242, 2002, pp. 313-317.

W. Chiou, et al., "Pharmaceutical Applications of Solid Dispersions Systems", Journal of Pharmaceutical Sciences, vol. 60, No. 9, Sep. 1971, pp. 1281-1302.

C. Leuner, et al, "Improving Drug Solubility for Oral Delivery Using Solid Dispersions", International Journal of Pharmaceutics, 50, 2000, pp. 47-60.

I. Utsumi, et al., 1983, pp. 157-159.

I. Sugimoto, et al., vol. 2, 1981, pp. 17-26.

U.S. Appl. No. 11/433,618, filed May 15, 2006, Ogawa, et al.

U.S. Appl. No. 11/441,106, filed May 26, 2006, Takahashi, et al.

English abstracts of Excerpt of previously filed reference Utsumi, et al., pp. 157-159, 1983.

English abstracts of Excerpt of previously filed reference Sugimoto et al., vol. 2, pp. 17-26, 1981.

Kozo Takayama, et al., "Factors Affecting the Dissolution of Ketoprofen from Solid Dispersions in Various Water-soluble Polymers", Chem. Pharm. Bull. (1982), 30(8), pp. 3013-3016.

Gakuji Kiyonaka, et al., "Application of Ultrasound Compacting to Solid Dispersion", 60 (2), 148-159, (2000).

Akihiko Hasegawa, et al., "Dissolution Mechanism of Solid Dispersions of Nifedipine with Enteric Coating Agents", 1985, 105(6), pp. 586-592.

A. A. Kassem, et al., "Enhancement of the Rate of Release of Acetohexamide from its Tablets by the Formation of Solid-Dispersion with Polymers", Bulletin of the Faculty of Pharmacy (Cairo University), (1982), Volume date 1982, 19(1), pp. 309-328.

J. Kerc, et al., Nifedipine Solid Dispersions with Polymeric Carriers Using Fusion Technique, the Second Central European Symposium on Pharmaceutical Technology, (1997), 48(Pos. Stev.), pp. 284-285.

Noriyuki Hirasawa, et al., "An Attempt to Stabilize Nilvadipine Solid Dispersion by the Use of Ternary Systems", Drug Development and Industrial Pharmacy, vol. 29, No. 9, pp. 997-1004, 2003.

English Excerpt from Office Action cited Japanese Patent Application No. 2005-515473 published May 26, 2005 (w/English Translation).

S.K. Joneja, et al., Investigating the Fundamental Effects of Binders on Pharmaceutical Tablet Performance, Drug Development and Industrial Pharmacy, 25 (10), 1129-1135 (1999).

\* cited by examiner

Test Example 6

SOLID DISPERSIONS OR SOLID DISPERSION PHARMACEUTICAL PREPARATIONS OF PHENYLALANINE DERIVATIVES

CROSS REFERENCES TO RELATED APPLICATIONS

This application is a continuation of International Patent Application No. PCT/JP04/16942, filed on Nov. 15, 2004, and claims priority to Japanese Patent Application No. 2003-385501, filed on Nov. 14, 2003.

TECHNICAL FIELD OF THE INVENTION

The present invention relates to solid dispersions or solid dispersion pharmaceutical preparations of phenylalanine derivatives or pharmaceutically acceptable salts thereof, which have an α 4 integrin inhibiting activity and are useful as agents for treating inflammatory bowel diseases and the like. Further, the present invention also relates to solubilized pharmaceutical preparations of the above derivatives or pharmaceutically acceptable salts thereof.

BACKGROUND OF THE INVENTION

Conventionally, it has been known that solubility or absorbability of poorly-soluble drugs is improved by dispersing the poorly-soluble drugs in polymers to form solid dispersions. For instance, there has been known that the solubility and the like are improved by dispersing Griseofulvin in polyethyleneglycol polymer that is a water-soluble polymeric substance to form a solid dispersion (Non-Patent Literature 1).

Incidentally, compounds of the formula (1), which are a subject of the present invention, or pharmaceutically acceptable salts thereof are the compounds which have an α 4 integrin inhibiting activity and are useful as agents for treating inflammatory bowel diseases and the like. Though they can be produced in accordance with the description of Patent Literature 1 and the publication discloses tablets, capsules, and the like wherein the compound of the formula (1) or pharmaceutically acceptable salts thereof are dispensed, there is no disclosure on solid dispersions or solid dispersion pharmaceutical preparations therein. There is no disclosure on solubilized pharmaceutical preparations, either. The compounds of the formula (1) or pharmaceutically acceptable salts thereof are poorly-soluble drugs and their solubility or absorbability needs to be improved.

[Patent Literature 1] WO02/16329
[Non-Patent Literature 1] J. Pharm. Sci., 60, 9, pp 1281-1302, (1971)

DISCLOSURE OF THE INVENTION

The object of the present invention is to provide a form wherein the solubility or absorbability of the compound of the formula (1) or pharmaceutically acceptable salts thereof is improved, and a pharmaceutical preparation thereof.

The inventors variously studied the above problem to solve it from the view of pharmaceutical preparation, and found that the solubility and absorbability of the compound of the formula (1) or pharmaceutically acceptable salts thereof is improved by treating the compounds in amorphous state with a water-soluble polymeric substance(s) to form a solid dispersion. The present invention has been completed based on this finding.

They also have found that the solubility and absorbability of the compound of the formula (1) or pharmaceutically acceptable salts thereof is improved by dissolving and dispersing the compounds in a solubilizer(s). The present invention has also been completed based on this finding. In this case, a surfactant(s) or a pharmaceutically acceptable oil(s) may be added to the compounds.

Namely, the present invention relates to a solid dispersion wherein a phenylalanine compound of the following formula (1) (hereinafter referred to as a compound (I)) or pharmaceutically acceptable salts thereof is dispersed in amorphous state in a water-soluble polymeric substance(s):

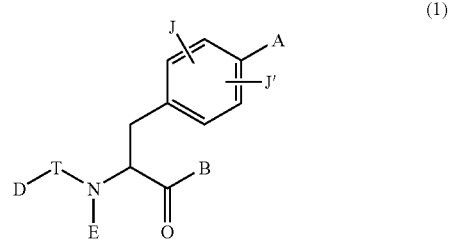

(1)

wherein A represents one of the following formulae (2), (3), (3-1) and (3-2):

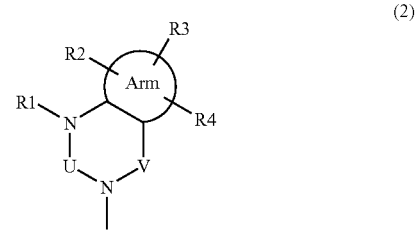

(2)

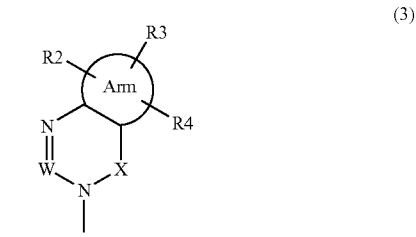

(3)

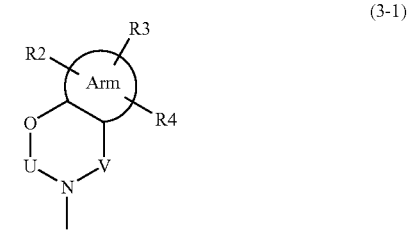

(3-1)

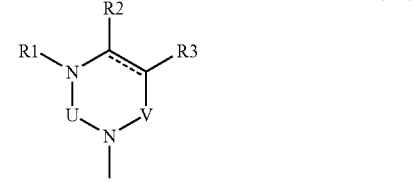

(3-2)

wherein Arm represents a cycloalkyl group or an aromatic ring containing 0, 1, 2, 3 or 4 hetero atoms selected from the group consisting of oxygen, sulfur and nitrogen atoms, the composite line of solid line and dotted line in the formula (3-2) represents a single bond or a double bond, U, V and X represent C(=O), S(=O)$_2$, C(—R5)(—R6), C(=C(R5)(R6)), C(=S), S(=O), P(=O)(—OH) or P(—H)(=O), W represents C(—R7) or a nitrogen atom, $R^1$, $R^2$, $R^3$, $R^4$ $R^5$, $R^6$ and $R^7$ may be the same or different from one another and each represent a hydrogen atom, a halogen atom, a hydroxyl group, a lower alkyl group, a substituted lower alkyl group, a lower alkenyl group, a substituted lower alkenyl group, a lower alkynyl group, a substituted lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxy group, a lower alkylthio group, a lower alkoxy group and lower alkylthio group substituted with a cycloalkyl group(s) which may contain a hetero atom(s) in the ring thereof, a lower alkoxy group and lower alkylthio group substituted with an aryl group(s), a lower alkoxy group and lower alkylthio group substituted with a heteroaryl group(s), a cycloalkyloxy group which may contain a hetero atom(s) in the ring thereof, an aryloxy group, a heteroaryloxy group, a hydroxy-lower alkyl group, a hydroxy-lower alkenyl group, a hydroxy-lower alkoxy group, a halogeno-lower alkyl group, a halogeno-lower alkoxy group, a halogeno-lower alkylthio group, a halogeno-lower alkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylsulfonyl group, a substituted or unsubstituted sulfamoyl group or an ammonium group, $R^5$ and $R^6$ may be bonded together to form a ring which may contain one or two oxygen, nitrogen or sulfur atoms, B represents a hydroxyl group, a lower alkoxy group or hydroxylamino group, E represents a hydrogen atom, a lower alkyl group, a lower alkenyl group, a lower alkynyl group, a lower alkyl group substituted with a cycloalkyl group(s) which may contain a hetero atom(s) in the ring thereof, a lower alkyl group substituted with an aryl group(s) or a lower alkyl group substituted with a heteroaryl group(s), D represents a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxy group, a lower alkoxy group substituted with a cycloalkyl group(s) which may contain a hetero atom(s) in the ring thereof, a lower alkoxy group substituted with an aryl group(s), a lower alkoxy group substituted with a heteroaryl group(s), a cycloalkyloxy group which may contain a hetero atom(s) in the ring thereof, an aryloxy group, a heteroaryloxy group, a hydroxy-lower alkyl group, a hydroxy-lower alkenyl group, a hydroxy-lower alkoxy group, a halogeno-lower alkyl group, a halogeno-lower alkoxy group, a halogeno-lower alkenyl group, a nitro group, a cyano group, a substituted or unsubstituted amino group, a carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group, E and D may be bonded together to form a ring which may contain one or two oxygen, nitrogen or sulfur atoms, T represents an interatomic bond, C(=O), C(=S), S(=O), S(=O)$_2$, N(H)—C(=O), or N(H)—C(=S), and J and J' may be the same or different from each other and each represent a hydrogen atom, a halogen atom, a lower alkyl group, a lower alkyloxy group or nitro group.

The present invention also relates to a solid dispersion pharmaceutical preparation which is prepared by processing the above solid dispersion with one or more steps selected from mixing, granulation, kneading, tableting, capsule filling, and coating.

Additionally, the present invention relates to a solid dispersion pharmaceutical preparation which is prepared by coating a core component containing the above solid dispersion with a coating agent(s).

The present invention further relates to a method for producing the solid preparation which adopts either one of steps of: (i) dissolving or dispersing the above compound (I) or pharmaceutically acceptable salts thereof in an organic solvent(s) together with a water-soluble polymeric substance(s), and then removing the organic solvent(s); (ii) dissolving or dispersing the above compound (I) or pharmaceutically acceptable salts thereof in a water-soluble polymeric substance(s) under heating, and then cooling the mixture; (iii) dissolving or dispersing the above compound (I) or pharmaceutically acceptable salts thereof in a water-soluble polymeric substance(s) under heating and under pressure, and then cooling the mixture; and (iv) mixing the above compound (I) or pharmaceutically acceptable salts thereof together with a water-soluble polymeric substance(s), and then grinding the mixture.

The present invention further relates to a solubilized pharmaceutical preparation containing a solubilizer(s) and the above compound (I) or pharmaceutically acceptable salts thereof.

BEST MODE FOR CARRYING OUT THE INVENTION

Figure 1:
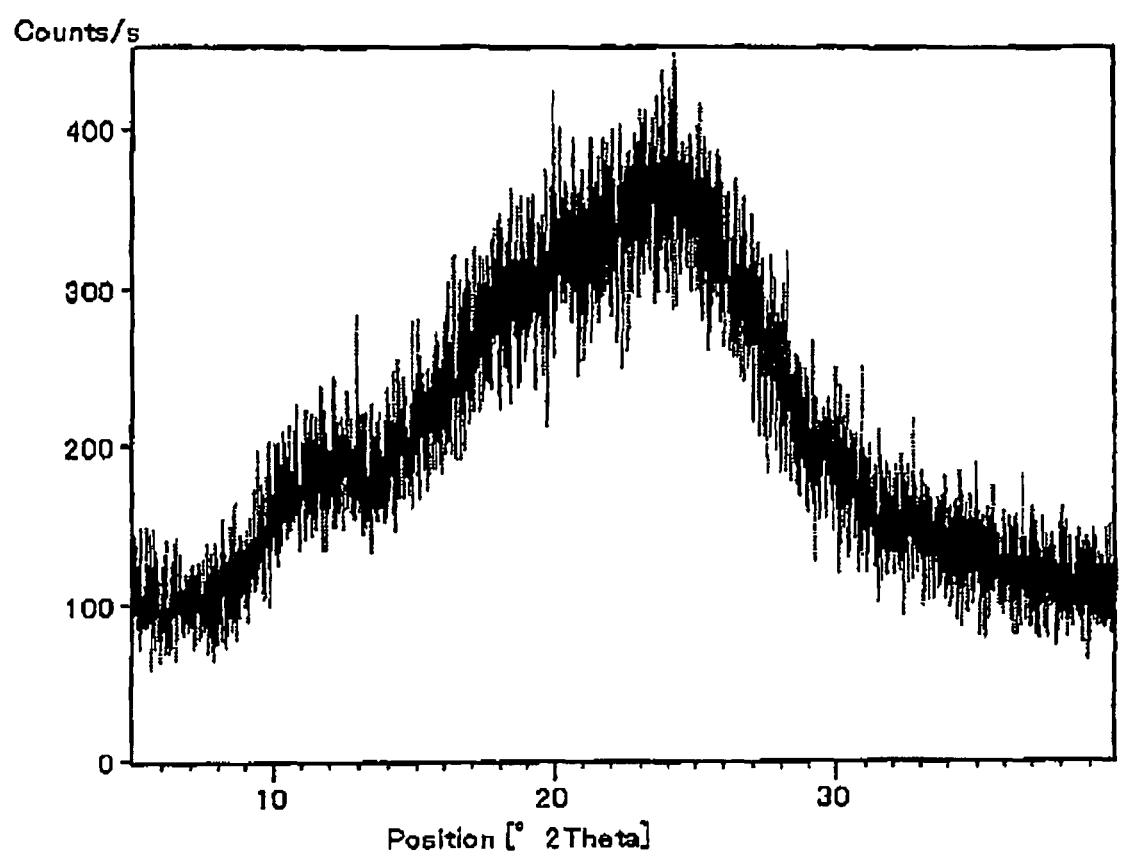
FIG. 1 shows an explanatory chart of the powder X-ray diffraction of Example 1.
Figure 2:
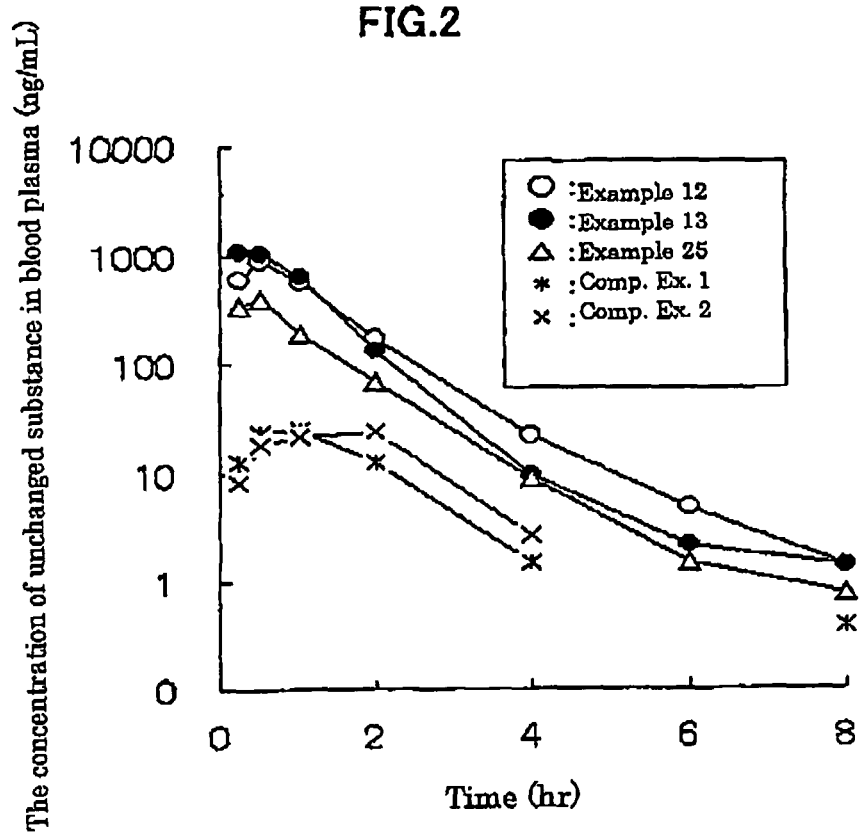
FIG. 2 shows an explanatory chart which indicates shifts of the concentration of the compound A in blood plasma when solid dispersions of Examples 12 and 13, a solubilized pharmaceutical preparation of Example 25, a suspension obtained in Comparative Example 1, and ordinary tablets obtained in Comparative Example 2 were administered to beagle dogs for oral administration.
Figure 3:
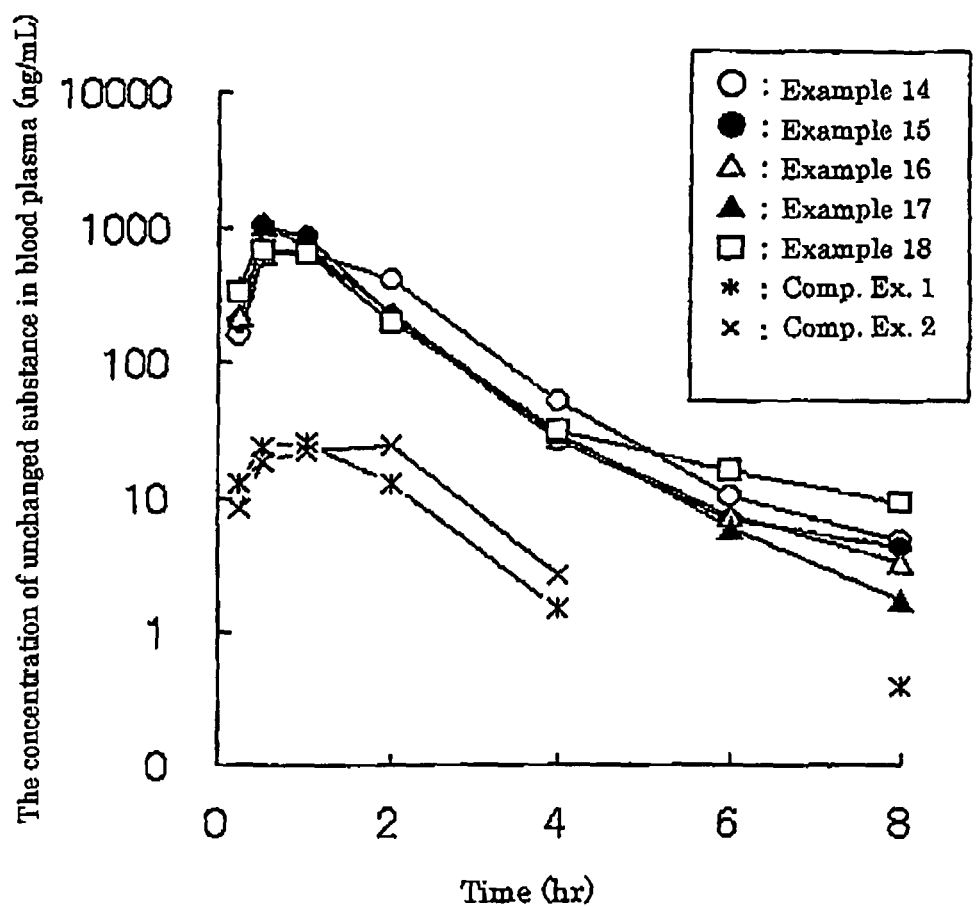
FIG. 3 shows an explanatory chart which indicates shifts of the concentration of the compound A in blood plasma when solid dispersion pharmaceutical preparations of Examples 14 to 18, a suspension obtained in Comparative Example 1, and ordinary tablets obtained in Comparative Example 2 were administered to beagle dogs for oral administration.
Figure 4:
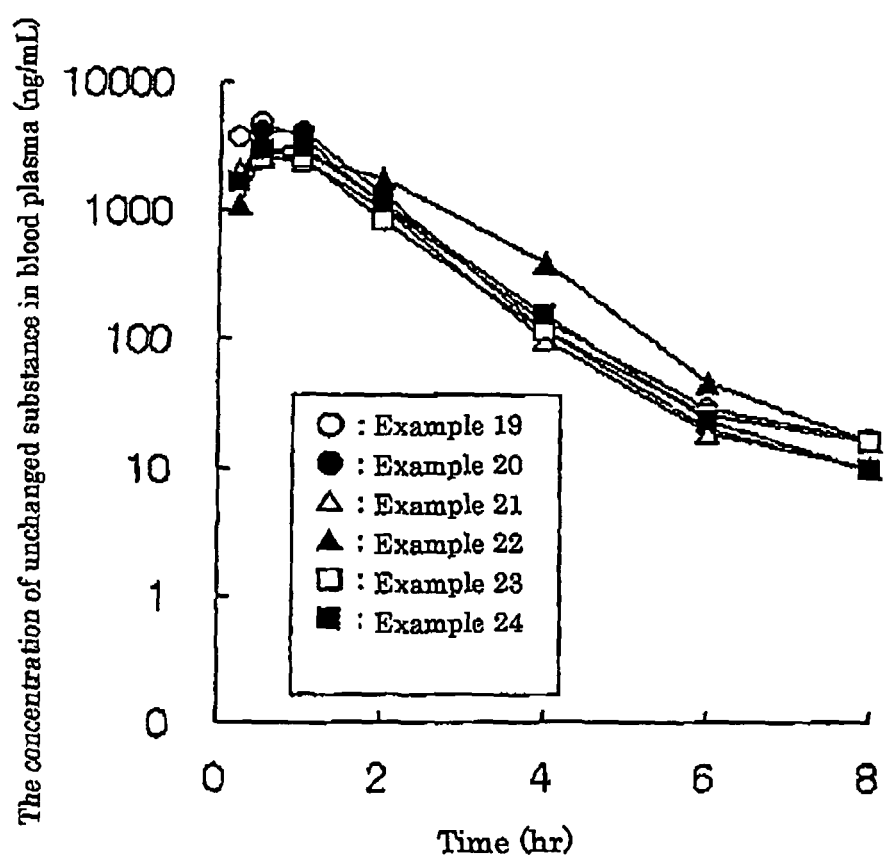
FIG. 4 shows an explanatory chart which indicates shifts of the concentration of the compound A in blood plasma when solid dispersion pharmaceutical preparations of Examples 19 to 24 were administered to beagle dogs for oral administration.
Figure 5:
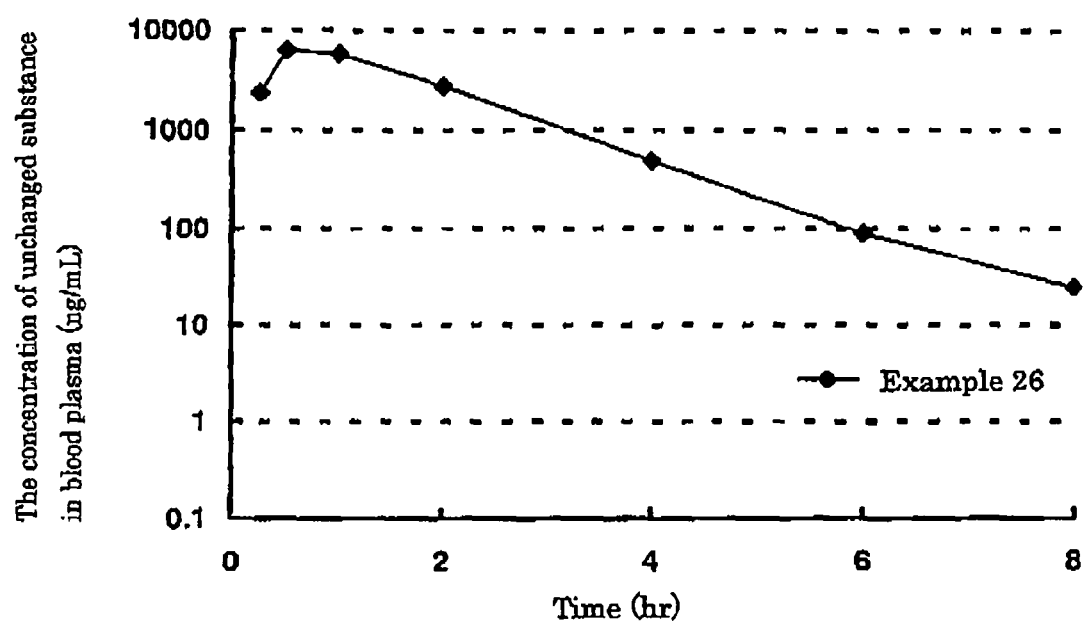
FIG. 5 shows an explanatory chart which indicates a shift of the concentration of the compound A in blood plasma when a solid dispersion pharmaceutical preparation of Example 26 was administered to beagle dogs for oral administration.

In the definition of each group in the formulae (1), (2), (3-1), and (3-2) in the present specification, the term "lower" in, for example, a lower alkyl group indicates that the group has 1 to 6 carbon atoms and preferably 1 to 4 carbon atoms. Alkyl groups per se and also alkyl groups in alkenyl groups, alkynyl groups, alkoxy groups, alkylthio groups, alkanoyl groups and alkylamino groups, alkenyl groups and alkynyl groups may be either linear or branched. Examples of these alkyl groups are a methyl group, ethyl group, propyl group, isopropyl group, butyl group, secondary butyl group, tertiary butyl group, pentyl group and hexyl group. It is preferable that the alkyl groups have 1 to 6 carbon atoms and more preferable that the groups have 1 to 4 carbon atoms. The alkenyl groups are, for example, a vinyl group, propenyl group, butenyl group and pentenyl group. It is preferable that the alkenyl groups have 2 to 6 carbon atoms and more preferable that the groups have 2 to 4 carbon atoms. The alkynyl groups include an ethynyl group, propynyl group and butynyl group. It is preferable that the alkynyl groups have 2 to 8 carbon atoms and more preferable that the groups have 2 to 4 carbon atoms. The cycloalkyl groups indicate substituted or unsubstituted cycloalkyl groups such as a cyclopropyl group, cyclobutyl group, cyclopentyl group, cyclohexyl group, norbornyl group, adamantyl group and cyclohexenyl group. It is preferable that the cycloalkyl groups have 3 to 8 carbon atoms and more preferable that the groups have 3 to 5 carbon atoms. The alkoxy groups include a methoxyl group, ethoxyl group, propyloxy group, isopropyloxy group, etc. It is preferable that the alkoxy groups have 1 to 6 carbon atoms and more preferable that the groups have 1 to 4 carbon atoms.

The hetero atoms include nitrogen, oxygen, sulfur, etc. The halogen atoms are fluorine, chlorine, bromine and iodine. The halogenoalkyl groups include a chloromethyl group, trichloromethyl group, trifluoromethyl group, trifluoroethyl group, pentafluoromethyl group, etc. The halogenoalkoxy groups include a trichloromethoxy group, trifluoromethoxy group, etc. The hydroxyalkyl groups include a hydroxymethyl group, hydroxyethyl group, etc. The cycloalkyl groups which may contain a hetero atom(s) in the ring thereof may be either substituted or unsubstituted. Examples of them include a cyclopentyl group, cyclohexyl group, piperidyl group, piperazinyl group, morpholinyl group, pyrrolidinyl group, tetrahydrofuranyl group and uracil group, which are preferably 4-to-8-membered cyclic group, and more preferably 5-to-7-membered cyclic group.

The aryl groups are both substituted and unsubstituted aryl groups such as a phenyl group, 1-naphthyl group and 2-naphthyl group. They are preferably a phenyl group and substituted phenyl group, and the substituents are particularly preferably halogen atoms, alkoxy groups, alkyl groups, hydroxyl group, halogenoalkyl groups and halogenoalkoxy groups. The heteroaryl groups are both substituted and unsubstituted heteroaryl groups such as a pyridyl group, pyrazyl group, pyrimidyl group, pyrazolyl group, pyrrolyl group, triazyl group, furyl group, thienyl group, isoxazolyl group, isothiazolyl group, indolyl group, quinolyl group, isoquinolyl group, benzimidazolyl group and imidazolyl group. Preferable heteroaryl groups are a pyridyl group, pyrazyl group, pyrimidyl group, furyl group, thienyl group, imidazolyl group and substituted pyridyl, furyl and thienyl groups. Particularly preferable substituents are halogen atoms, alkoxy groups, alkyl groups, hydroxyl group, halogenoalkyl groups and halogenoalkoxy groups. The lower alkyl groups substituted with an aryl group(s) include, for example, substituted or unsubstituted benzyl groups and substituted or unsubstituted phenethyl groups. Particularly preferable substituents are halogen atoms, alkoxy groups, alkyl groups, hydroxyl group, halogenoalkyl groups and halogenoalkoxy groups. The lower alkyl groups substituted with a heteroaryl group(s) include, for example, a pyridylmethyl group, and particularly preferable substituents thereof are halogen atoms, alkoxy groups, alkyl groups, hydroxyl group, halogenoalkyl groups and halogenoalkoxy groups.

The alkanoyl groups include, for example, a formyl groups, acetyl groups, propanoyl group, butanoyl group and pivaloyl group. The aroyl groups include, for example, substituted or unsubstituted benzoyl groups and a pyridylcarbonyl group, and the substituents thereof are particularly preferably halogen atoms, alkoxy groups, alkyl groups, hydroxyl group, halogenoalkyl groups and halogenoalkoxy groups. The halogenoalkanoyl groups include, for example, a trichloroacetyl group and trifluoroacetyl group. The alkylsulfonyl groups include, for example, a methanesulfonyl group, ethanesulfonyl group, etc. The arylsulfonyl groups include, for example, a benzenesulfonyl group and p-toluenesulfonyl group. The heteroarylsulfonyl groups include, for example, a pyridylsulfonyl group. The halogenoalkylsulfonyl groups include, for example, a trifluoromethanesulfonyl group. The alkyloxycarbonyl groups include, for example, a methoxycarbonyl group, ethoxycarbonyl group and tert-butoxycarbonyl group. The aryl-substituted alkoxycarbonyl groups include, for example, a benzyloxycarbonyl group and 9-fluorenylmethoxycarbonyl group.

The substituted carbamoyl groups include, for example, a methylcarbamoyl group, phenylcarbamoyl group and substituted phenylcarbamoyl group, and the substituents thereof are particularly preferably halogen atoms, alkoxy groups, alkyl groups, hydroxyl group, halogenoalkyl groups and halogenoalkoxy groups. The substituted thiocarbamoyl groups include, for example, a methylthiocarbamoyl group, phenylthiocarbamoyl group and substituted phenylthiocarbamoyl groups, and the substituents thereof are particularly preferably halogen atoms, alkoxy groups, alkyl groups, hydroxyl group, halogenoalkyl groups and halogenoalkoxy groups. The substituted amino groups herein indicate mono-substituted or di-substituted amino groups and the substituents thereof include lower alkyl groups, lower alkyl groups substituted with an aryl group, lower alkyl groups substituted with a heteroaryl group, lower alkanoyl groups, aroyl groups, halogeno-lower alkanoyl groups, lower alkylsulfonyl groups, arylsulfonyl groups, heteroarylsulfonyl groups, halogenoalkylsulfonyl groups, lower alkyloxycarbonyl groups, aryl-substituted lower alkyloxycarbonyl groups, substituted or unsubstituted carbamoyl groups and substituted or unsubstituted thiocarbamoyl groups. The ammonium groups include such as trialkylammonium groups.

Because the phenylalanine compounds of the formula (1) of the present invention include asymmetric carbons, it is thinkable that the compounds are optical isomers and the compounds indicated in the present invention include the said optical isomers. However, L-form is preferable.

Regarding the compounds in which a diastereomer exists, the diastereomer and the diastereomer compound are included in the said phenylalanine compounds. Because the phenylalanine compounds of the formula (1) of the present invention include a mobile hydrogen atom, it is thinkable that the compounds of the present invention are a variety of tautomeric forms and the compounds indicated in the present invention include the said tautomeric forms. Further, the carboxyl groups of the compound of the present invention may be substituted with appropriate substituents which are converted into a carboxyl group in vivo. An example of such substituents is a lower alkoxycarbonyl group.

When the compounds of the formula (1) of the present invention can form salts thereof, the salts are pharmaceutically acceptable ones. When the compound has an acidic group such as carboxyl group in the formula, the salts can be salts thereof with alkali metals, e.g. sodium, potassium and ammonium, salts thereof with alkaline earth metals, e.g. calcium and magnesium, salts thereof with aluminum and zinc, salts thereof with organic amines, e.g. triethylamine, ethanolamine, morpholine, piperidine and dicyclohexylamine, and salts thereof with basic amino acids, e.g. arginine and lysine. When the compound has a basic group in the formula, the salts can be those with inorganic acids, e.g. hydrochloric acid, sulfuric acid and phosphoric acid; those with organic carboxylic acids, e.g. acetic acid, citric acid, benzoic acid, maleic acid, fumaric acid, tartaric acid and succinic acid; and those with organosulfonic acids, e.g. methanesulfonic acid and p-toluenesulfonic acid. The salts can be formed by mixing a compound of the formula (1) with a necessitated acid or base in a proper ratio in a solvent or dispersing agent or by the cation exchange or anion exchange reaction with another salt.

The compounds of the formula (1) of the present invention include also solvates thereof such as hydrates and alcohol adducts thereof.

The compound (I) or pharmaceutically acceptable salts thereof can be produced by the method described in WO02/16329 (Patent Literature 1). The description of WO002/16329 is included in that of the present specification. The concrete examples of the compound (I) include Examples 1 to 213 described in WO02/16329 (Patent Literature 1).

In the compound (I) or pharmaceutically acceptable salts thereof, the phenylalanine compound of the formula (1) is preferably a compound wherein R1 represents a methyl group or an ethyl group; and R2, R3, and R4 represent a hydrogen atom, a halogen atom, a hydroxyl group, a substituted low alkyl group, a substituted lower alkenyl group, a substituted lower alkynyl group, a heteroaryl group, a hydroxy-lower alkyl group, an amino group substituted with a lower alkyl group, or a carbamoyl group substituted with a lower alkyl group, wherein the substituents in the substituted low alkyl group, the substituted lower alkenyl group and the substituted lower alkynyl group include an amino group, an amino group substituted with a lower alkyl group, a carboxyl group, a lower alkoxycarbonyl group, a cyano group, a lower alkylthio group, and a lower alkylsulfonyl group.

The compound (I) or pharmaceutically acceptable salts thereof are preferably Examples 1, 108, 162, 169, 122, 66, 91, 99, 89, 75, 147, 148, 202, 201, 196, 193, 198 or 197 described in WO02/16329 (Patent Literature 1). They are shown as follows.

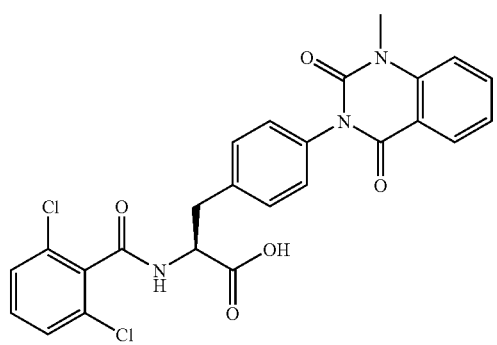

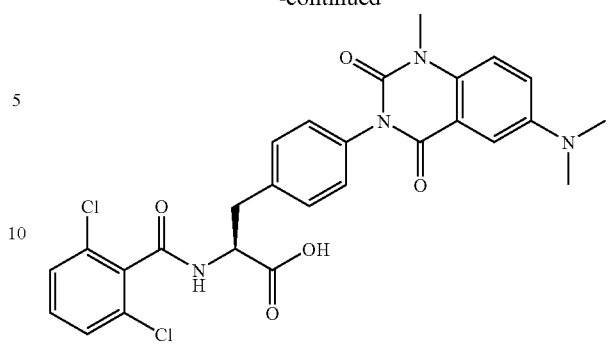

-continued

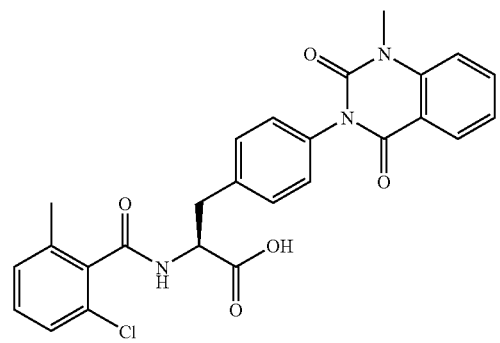

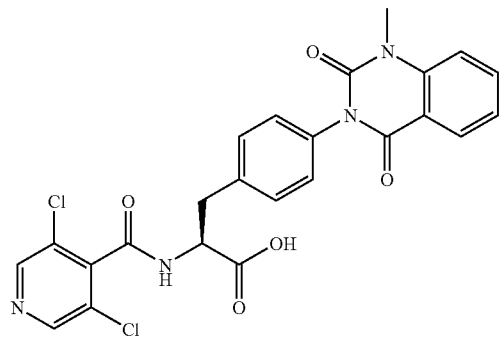

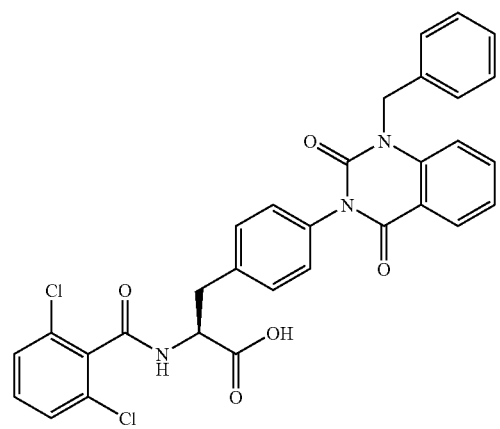

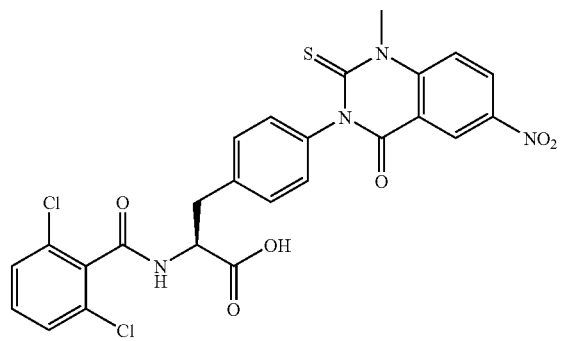
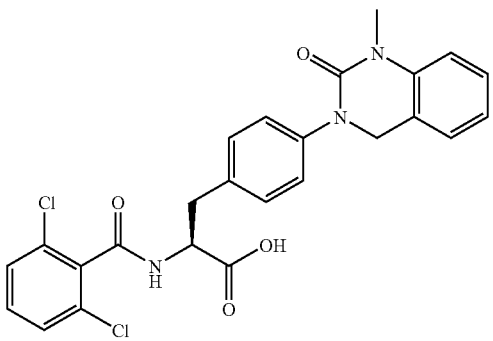
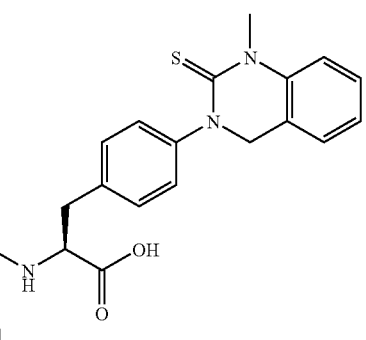
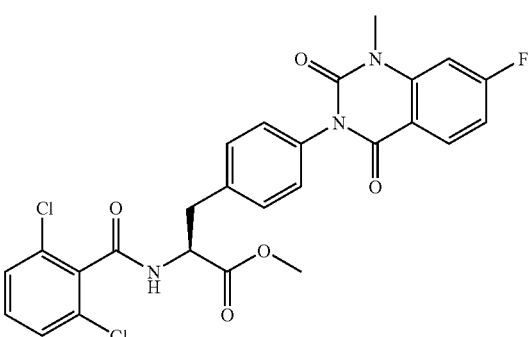
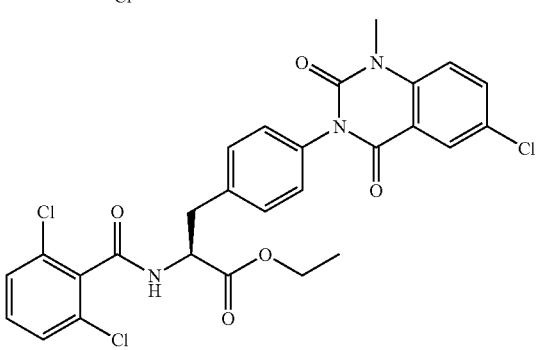
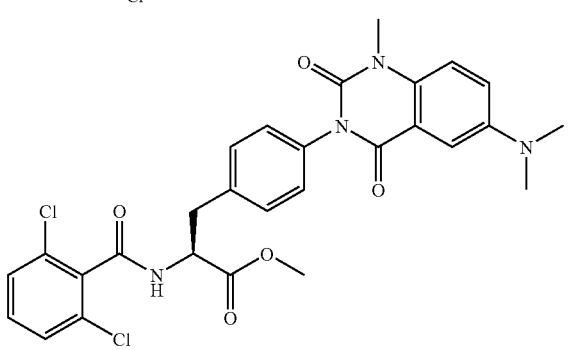

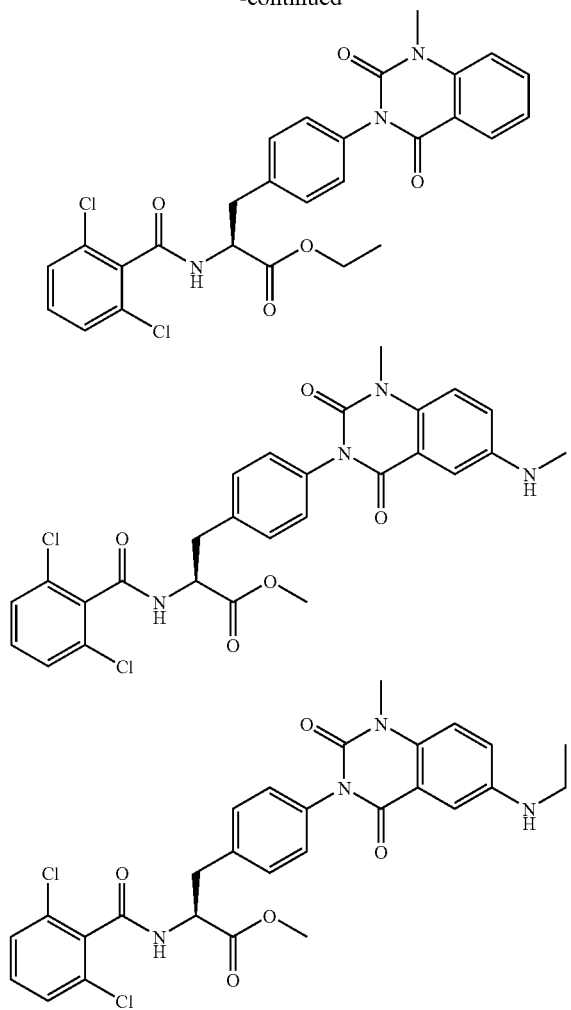

Most preferable one is Example 196 described in WO02/16329 (Patent Literature 1). The present compound (hereinafter referred to as a compound (A)) is shown as follows.

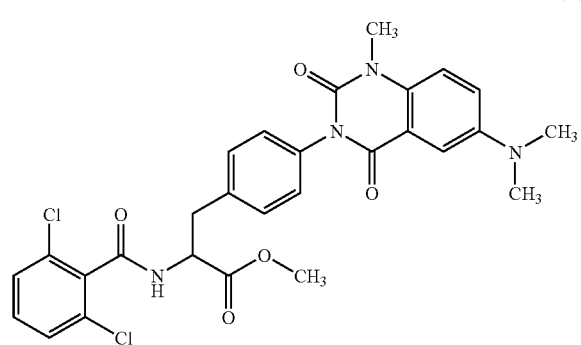

(A)

The "solid dispersions" in the present invention are those wherein drugs are dispersed in amorphous state in a water-soluble polymeric substance(s). It has been found that such forms can improve the solubility of drugs in the present invention. By forming solid dispersions, it is preferable that the solubility of such drugs in the phosphate buffer (pH 6.8) described in USP (the United States Pharmacopoeia) 24 increases by 1.5-fold and more preferably by 2-fold or higher than that of the drugs per se. Here, the solubility can be determined, for example, by keeping 500 mL of the phosphate buffer (pH 6.8) described in USP 24 to 37±0.5° C.; adding thereto about 20 mg of the compound (I) as a solid dispersion; and measuring the dissolution quantity of the drug in 50 rpm 60 minutes later.

The water-soluble polymeric substances usable in the present invention are those which are soluble in water and can dissolve or disperse the compound (I) or pharmaceutically acceptable salts thereof, and they are not particularly limited. Various synthetic polymers and natural polymers are used. The water-soluble polymeric substances include celluloses and derivatives thereof, e.g. methylcellulose, hydroxypropylmethylcellulose, hydroxypropylcellulose, hydroxypropylmethylcellulose phthalate, hydroxypropylmethylcellulose acetate succinate, carboxymethylethylcellulose, carboxylmethylcellulose sodium, hydroxyethylcellulose, and cellulose acetate phthalate; synthetic polymers, e.g. polyethyleneglycol, polyvinyl alcohol, polyvinylpyrrolidone, polyvinylacetal diethylaminoacetate, aminoalkyl methacrylate copolymer E, aminoalkyl methacryl copolymer RS, methacrylic acid copolymer L, methacrylic acid copolymer LD, methacrylic acid copolymer S, and carboxylvinyl polymer; and natural polymers and sugars, e.g. gum arabic, sodium alginate, propylene glycol alginate, agar, gelatin, tragacanth, and xanthan gum as preferable examples.

The water-soluble polymeric substances include methylcellulose, hydroxypropylmethylcellulose, hydroxypropylcellulose, polyethyleneglycol, polyvinyl alcohol, polyvinylpyrrolidone, and the like, and methylcellulose and hydroxypropylmethylcellulose are particularly preferably used. These polymeric substances can be used by its own or by mixture.

In the solid dispersions or solid dispersion pharmaceutical preparations of the present invention, the ratio between the compound (I) and the water-soluble polymeric substance(s) is preferably 0.1 to 100 parts by weight of the latter to 1 part by weight of the former, more preferably 0.25 to 20 parts by weight thereof and further more preferably selected from the range of 0.5 to 10 parts by weight thereof.

The solid dispersions of the present invention can be prepared, for example, by a solvent method, a melt method, a melt-kneading method under heating and pressure, or a mixing grinding method.

The solvent method is the method that the compound (I) or pharmaceutically acceptable salts thereof are dissolved or dispersed in an organic solvent(s) together with a water-soluble polymeric substance(s), and then the organic solvent(s) is removed in accordance with the ordinary methods.

The methods for dissolving or dispersing the compounds in an organic solvent(s) are:

(i) dissolving or dispersing the compound (I) or pharmaceutically acceptable salts thereof by themselves in an organic solvent(s), and further dispersing this solution in a water-soluble polymeric substance(s); and (ii) dissolving or dispersing the compound (I) or pharmaceutically acceptable salts thereof together with a water-soluble polymeric substance(s) in the organic solvent(s).

The organic solvents used in the solvent method are the solvents that dissolve or disperse the compound (I) or pharmaceutically acceptable salts thereof, and not particularly limited. The organic solvents include aliphatic halogenated hydrocarbons, e.g. dichloromethane, dichloroethane and chloroform; alcohols, e.g. methanol, ethanol and propanol;

ketones, e.g. acetone and methylethylketone; ethers, e.g. diethylether and dibutylether; aliphatic hydrocarbons, e.g. n-hexane, cyclohexane and n-heptane; aromatic hydrocarbons, e.g. benzene, toluene and xylene; organic acids, e.g. acetic acid and propionic acid; esters, e.g. ethyl acetate; amides, e.g. dimethylformamide and dimethylacetamide; and mixed solvents thereof. The halogenated hydrocarbons, alcohols and the mixed solvents thereof are preferable among them. Dichloromethane, methanol, ethanol and the mixed solvents thereof are further more preferable among them.

The organic solvents used in the solvent method also include mixed solvents of the above organic solvents and water.

The methods for dispersing and adsorbing the compound (I) or pharmaceutically acceptable salts thereof to a water-soluble polymeric substance(s) include the method comprising the steps of: dissolving the compound (I) or pharmaceutically acceptable salts thereof in an organic solvent(s), further dissolving or dispersing a water-soluble polymeric substance(s) in the organic solvent(s), and then removing the organic solvent(s) under reduced pressure or normal pressure in accordance with ordinary methods; or that comprising the steps of: dissolving the compound (I) or pharmaceutically acceptable salts thereof in an organic solvent(s), further dissolving or dispersing a water-soluble polymeric substance(s) in the organic solvent(s), granulating or mixing the mixed solution together with auxiliaries such as diluents and disintegrant using agitation granulators, fluid bed granulators, spraydryers, Bohle container mixer, V-mixers and the like, and then removing the organic solvent(s) under reduced pressure or normal pressure in accordance with ordinary methods.

Removal of an organic solvent(s) can be conducted, for example, by drying under reduce pressure or drying under heating. The conditions such as the treatment pressure, temperature and time vary depending on used compounds, water-soluble polymeric substances, organic solvents and the like. The treatment pressure is within the range of 1 mmHg to normal pressure; the treatment temperature is within the range of room temperature to 250° C.; and the treatment time is within the range of a few minutes to several days.

The melt method is the method that the compound (I) or pharmaceutically acceptable salts thereof are dissolved or dispersed under heating in a water-soluble polymeric substance(s) and then cooled down. The methods for dissolving or dispersing the compounds include stirring by heating the compounds up to or higher than the melting point or the softening point of the compound (I) or pharmaceutically acceptable salts thereof or those of the water-soluble polymeric substance(s). In this case, plasticizers, e.g. polyethyleneglycol, sucrose fatty acid ester, glycerine fatty acid ester, propylene glycol, triethyl citrate, caster oil and triacetin; and surfactants, e.g. sodium lauryl sulfate, polysolvate 80, sucrose fatty acid ester, polyoxyl 40 stearate, polyoxyethylene 60 hydrogenated caster oil, sorbitan monostearate, and sorbitan monopalmitate can be added thereto as additives.

The solid dispersion pharmaceutical preparations by the melt method can be produced using agitation granulators with heating, for example.

More concretely, a mixture of a water-soluble polymeric substance(s) and the compound (I) or pharmaceutically acceptable salts thereof is prepared in advance. The above plasticizers or surfactants may be added to the mixture, if necessary. The conditions such as the treatment temperature and time vary depending on used compounds, water-soluble polymeric substances, additives and the like. The treatment temperature is within the range of room temperature to 300° C.; and the treatment time is within the range of a few minutes to ten and several hours. The cooling temperature is within the range of −100° C. to room temperature.

The melt-kneading method under heating and pressure is the method that the compound (I) or pharmaceutically acceptable salts thereof and a water-soluble polymeric substance(s) are mixed under heating and pressure. The conditions such as the treatment screw rotation speed, temperature and time vary depending on used compounds, water-soluble polymeric substances, additives and the like. The treatment screw rotation speed is within the range of 10 to 500 rpm; the treatment temperature is within the range of room temperature to 300° C.; and the treatment time is within the range of a few minutes to ten and several hours. The solid dispersions by the melt-kneading method under heating and pressure are produced using double-shaft kneading extruders with a heating device and kneading machines, for example. More concretely, for instance, they are produced by the following method.

The compound (I) or pharmaceutically acceptable salts thereof and a water-soluble polymeric substance(s), and the above additives, if necessary, are mixed in advance. The mixture is provided at the speed of powder supply of 10 to 200 g/min. The treatment is conducted in the conditions of: the treatment screw rotation speed of 50 to 300 rpm; and the treatment temperature of 25 to 300° C. This plastic-like solid dispersion is ground by a mill to obtain a solid dispersion.

The mixing grinding method is the method that the compound (I) or pharmaceutically acceptable salts thereof are mixed with a water-soluble polymeric substance(s) and then they are milled so that the compound (I) or pharmaceutically acceptable salts thereof become in amorphous state.

Mixing and milling are conducted using mixers and mills in accordance with ordinary methods. Here, milling of water-soluble polymers and the compound (I) is preferably conducted by cutter mills, ball mills, hammer mills, mortars and the like.

The solid dispersions of the present invention can be used as powders, fine granules or granules without change, or they can be further prepared in accordance with ordinary methods as solid dispersion pharmaceutical preparations such as tablets and capsules via processes for producing preparations (e.g. mixing, granulating, kneading, tableting, capsule filling, and coating). The mixing indicates, for example, the process where the solid dispersions of the present invention are mixed with other compounds by mixers. The granulating indicates, for example, the process where the solid dispersions of the present invention are granulated by agitation granulators. The kneading indicates, for instance, the process where the solid dispersions of the present invention are kneaded by kneading machines. The tableting indicates, for instance, the process where the solid dispersions of the present invention are prepared as tablets by tableting machines. The capsule filling indicates, for example, the process where the solid dispersions of the present invention are filled in capsules by capsule filling machines. The coating indicates, for example, the process where the solid dispersions of the present invention are coated with coating agents by coating machines.

When preparing drugs, if necessary, additives can be added thereto, such as diluents like sugars, e.g. lactose, sucrose, glucose, reduced maltose, mannitol, sorbitol, xylitol and trehalose, starches and derivatives thereof, e.g. partially α starch, dextrin, pullulan, corn starch and potato starch, celluloses, e.g. crystalline cellulose, microcrystalline cellulose, crystalline cellulose/carmellose sodium and hydroxypropyl cellulose, magnesium aluminometasilicate, silicon dioxide, light anhydrous silicic acid, and amino acids; coloring agents; flavoring agents, e.g. sucrose, aspartame, mannitol, dextran, saccharin, menthol, citric acid, tartaric acid, malic acid, ascorbic acid, sweet hydrangea leaves, fennel, ethanol, fructose, xylitol, glycyrrhizinic acid, purified sucrose, L-glutamine and cyclodextrin; disintegrants, e.g. hydroxypropyl cellulose, low-substituted hydroxypropyl cellulose, croscarmellose sodium, α starch, methylcellulose, sodium alginate, sodium carboxymethyl starch, carmellose calcium, carmellose sodium, crystalline cellulose and crystalline cellulose/carmellose sodium; lubricants, e.g. magnesium stearate, talc, light anhydrous silicic acid, calcium stearate, magnesium oxide, sodium lauryl sulfate and magnesium aluminometasilicate; and surfactants, e.g. sodium lauryl sulfate, polysolvate 80, sucrose fatty acid ester, polyoxyl 40 stearate, polyoxyethylene 60 hydrogenated caster oil, sorbitan monostearate and sorbitan monopalmitate.

In the solid dispersion pharmaceutical preparations of the present invention, the core component containing the solid dispersion may be particles of the solid dispersion itself or a substance wherein the solid dispersion is granulated with other components for preparation.

When the core component is the solid dispersion itself, the solid dispersion is preferably milled to be granulated. When the core component is the substance wherein the solid dispersion is granulated with other components for preparation, it is preferably granulated by mixing, fluid bed, extruding, and spraydrying with agitation granulators, fluid bed granulators, extruding granulators, Bohle container mixer, V-mixers, spraydryers and the like.

The solid dispersion pharmaceutical preparations of the present invention may contain foaming agents, and such preparations containing foaming agents are preferable in the solid dispersion pharmaceutical preparations of the present invention.

The forming agents are not particularly limited in the present invention and usually preferably consist of a reagent acting as a carbon dioxide source and a reagent inducing release of carbon dioxide. The reagents acting as a carbon dioxide source include monobasic or dibasic salts of pharmaceutically acceptable carbonic acids such as alkali metal carbonates, e.g. sodium carbonate, potassium carbonate, sodium hydrogen carbonate and potassium hydrogen carbonate, or alkali metal bicarbonates; alkali earth metal carbonates, e.g. calcium carbonate, magnesium carbonate and barium carbonate; and sodium glycine carbonate. These monobasic or dibasic salts of carbonic acids may be used by itself or by mixing two or more of them. Sodium hydrogen carbonate is preferable among them. The reagents inducing release of carbon dioxide include pharmaceutically acceptable organic acids and salts and acid anhydrides thereof such as succinic acid, tartaric acid, citric acid, malic acid, ascorbic acid, maleic acid, fumaric acid, adipic acid, anhydrides of citric acid, anhydrides of succinic acid, monosodium citrate, disodium citrate, sodium dihydrogenphosphate, oxalic acid and potassium dihydrogen phosphate. They may be used by itself or by mixing two or more of them. Tartaric acid, citric acid and ascorbic acid are preferable among them and tartaric acid is particularly preferable among them.

In the solid dispersions or the solid dispersion pharmaceutical preparations of the present invention, the ratio between the compound (A) and the foaming agents is preferably 0.001 to 200 parts by weight of the latter to 1 part by weight of the former, more preferably 0.01 to 1 parts by weight thereof and further more preferably selected from the range of 0.06 to 50 parts by weight thereof.

Further, the ratio between monobasic or dibasic salts of carbonic acids as reagents acting as a carbon dioxide source and organic acids and salts thereof and acid anhydrides is preferably 0.01 to 100 parts by weight of the latter to 1 part by weight of the former, more preferably 0.1 to 50 parts by weight thereof and further more preferably selected from the range of 0.25 to 25 parts by weight thereof. The methods for mixing monobasic or dibasic salts of carbonic acids with organic acids and salts and acid anhydrides thereof are preferably mixing with Bohle container mixer and V-mixers or shaking by hands.

In the solid dispersion pharmaceutical preparations of the present invention, the pharmaceutical preparations may be prepared by adding foaming agents to the solid dispersions and then tableting. The methods for adding the foaming agents include adding thereof together with a raw material and components for preparation during granulation, and mixing thereof in the obtained granules after the granulation.

When the obtained granules and foaming agents are granulated together, they can be granulated by agitation ganulation, fluid bed granulation, extruding granulation, and spray-drying with agitation granulators, fluid bed granulators, extruding granulators, and spray-dryers and the like. In case of adding foaming agents to the obtained granules after the granulation, it is preferable that they are mixed by Bohle container mixer, V-mixers, agitation granulators, and fluid bed granulators.

After that, the following coating agents may be applied thereto.

In the solid dispersion pharmaceutical preparations of the present invention, any coating agents are usable if they are regularly used in the pharmaceutical field. They include acrylic acid derivatives, e.g. methacrylic acid copolymer L, methacrylic acid copolymer S, methacrylic acid copolymer LD and aminoalkyl methacrylate copolymer E; cellulose derivatives, e.g. hydroxypropylmethylcellulose phthalate, hydroxypropylmethylcellulose acetate succinate, carboxymethylethylcellulose, cellulose acetate phthalate, hydroxyethylcellulose, hydroxypropylcellulose, hydroxypropylmethylcellulose, methylcellulose, methylhydroxyethylcellulose, opadry, carmellose calcium and carmellose sodium; vinyl derivatives, e.g. polyvinylpyrrolidone, polyvinyl alcohol and polyvinylacetal diethylaminoacetate; starches, e.g. dextrin and pullulan; and natural polymers and sugars, e.g. shellac, gelatin, agar and gum Arabic. One or more of these coating bases can be used.

They are preferably aminoalkyl methacrylate copolymer E, hydroxypropylmethylcellulose, methylcellulose, methylhydroxyethylcellulose, opadry, carmellose calcium and carmellose sodium, polyvinylpyrrolidone, polyvinyl alcohol, dextrin, pullulan, gelatin, agar and gum Arabic.

In coating, plasticizers, e.g. polyethyleneglycol, sucrose fatty acid ester, glycerine fatty acid ester, propylene glycol, triethyl citrate, caster oil and triacetin; or light shielding agents, e.g. titanium oxide and iron sesquioxide can be combined with coating agents in order to assist film forming property of film base materials and give new features.

Here, the coating quantity is within the amount by which the dissolution rate of the solid dispersion does not change drastically. The coverage of the solid part of the preparation is, for example, 0.1 to 20 weight %, preferably 0.5 to 10 weight % and more preferably 1 to 7 weight %.

The solubilized pharmaceutical preparations of the present invention are those that contain a solubilizer(s) and the compound (I) or pharmaceutically acceptable salts thereof, and they may further contain a surfactant(s) or pharmaceutically acceptable oils therein.

The solubilizers in the solubilized pharmaceutical preparations include propylene carbonate, propylene glycol, and polyethyleneglycols such as polyethyleneglycol 600, triethyl citrate, glycerin monofatty acids, e.g. glycerin monocaprate and glycerin monooleate, tricapryline, polysolvate 80, lauromacrogol, polyoxyethylene hydrogenated caster oils, glycerin, olive oil, sorbitan oleate ester, sorbitan laurate ester, diethylene glycol monoethyl ether, medium-chain triglyceride, oleyl alcohol, oleic acid, capric acid, hydrochloric acid, and lactic acid. They are preferably propylene carbonate, propylene glycol, polyethyleneglycols, triethyl citrate, glycerin monocaprate, and glycerin monooleate among them.

As the surfactants in the solubilized pharmaceutical preparations, nonionic surfactants, ionic surfactants, and hydrophobic surfactants can be used.

The nonionic surfactants include polyoxyethylene surfactants, e.g. polyoxyethylene alkylether, polyoxyethylene alkylphenol, polyoxyethylene hydrogenated caster oil, polyoxyethylene monofatty acid, polyoxyethylene monopolyoxyethylene glycol fatty acid ester, polyoxyethylene glyceol fatty acid ester, polyoxyethylene sorbitan fatty acid ester, polyoxyethylene-polyoxypropylene glycol polyoxyethylene glyderide, polyoxyethylene sterol, polyoxyethylene vegetable oil and polyoxyethylene hydrogenated vegetable oil; alkyl glucoside, alkyl maltoside, alkyl thioglucoside, lauryl macrogolglyceride, polyglyceol fatty acid ester, saccharose ester, saccharose ether and glyceride. Further, they also include the reaction mixture of polyalcohols and at least one kind selected from the group consisting of fatty acid, glyceride, vegetable oil, hydrogenated vegetable oil and sterol.

The ionic surfactants include bile salts, amino acids, alkylammonium salts, fatty acid condensation products of oligopeptides or polypeptides, phospholipids and lysophospholipids.

The hydrophobic surfactants include polyoxyethylene alkylether, bile acid, acetylated glyceol fatty acid ester, lactic acid ester, and propyleneglycol diglyceride.

The polyoxyethylene surfactants are preferable among them, and polyoxyethylene hydrogenated caster oils, e.g. polyoxyethylene 50, 60, 100 hydrogenated caster oils (HCO50, 60, 100); polyoxyethylene monofatty acids, e.g. polyoxyl 40 stearate; and polyoxyethylene-polyoxypropylene glycols, e.g. pluronic and PEP101.

The pharmaceutically acceptable oils in the solubilized pharmaceutical preparations include myristic acid, oleic acid, soybean oil, sorbitan monofatty acids such as sorbitan monooleate, glycerin esters of fatty acids such as oleic acid glycerin ester, caprylic acid glycerin ester and laurylic acid glycerin ester, and polyoxyethylene hydrogenated caster oils such as polyoxyethylene 10 hydrogenated caster oil and polyoxyethylene 30 hydrogenated caster oil.

They are preferably glycerin esters of fatty acids having 6 to 18 carbon atoms such as oleic acid glycerin ester, caprylic acid glycerin ester and laurylic acid glycerin ester, and polyoxyethylene hydrogenated caster oils such as polyoxyethylene 10 hydrogenated caster oil and polyoxyethylene 30 hydrogenated caster oil.

Though the solubilizers have a solubilizing effect by themselves, they are preferably used in combination with pharmaceutically acceptable surfactants or oils.

The solubilized pharmaceutical preparations are preferably those prepared in combination with (i) polyoxyethylene surfactants and (ii) either one of pharmaceutically acceptable oils selected from glycerin esters of fatty acids having 6 to 18 carbon atoms, polyoxyethylene hydrogenetated caster oils, sorbitan fatty acid esters, and propylene glycol fatty acid esters.

The solubilized pharmaceutical preparations are furthermore preferably those prepared in combination with (i) polyoxyethylene 60 hydrogenated caster oil and (ii) either one of pharmaceutically acceptable oils selected from oleic acid glycerin esters, caprylic acid glycerin esters and laurylic acid glycerin esters, polyoxyethylene 10 hydrogenated caster oil and polyoxyethylene 30 hydrogenated caster oil.

The ratios of each components of the compound (I) or pharmaceutically acceptable salts thereof, surfactants, solubilizers, and pharmaceutically acceptable oils are, when regarding the compound (I) or pharmaceutically acceptable salts thereof as 1, that the solubilizers are within the weight ratio of 1 to 100; the surfactants are within the weight ratio of 0.1 to 20; and the pharmaceutically acceptable oils are within the weight ratio of 0.01 to 20.

The methods for producing the solubilized pharmaceutical preparations include the method that the compound (I) or pharmaceutically acceptable salts thereof are dispersed and dissolved in a solubilizer(s) using agitator, homogenizers, high-pressure homogenizers or ultrasonic homogenizers to produce the preparations. In case of containing surfactants or pharmaceutically acceptable oils, there is the method that the surfactants or the pharmaceutically acceptable oils are added and mixed to the compound (I) or pharmaceutically acceptable salts thereof and a solubilizer(s) to produce the preparations.

The solubilized pharmaceutical preparations are preferably administered as solutions, emulsions, preparations filled in capsules, or preparations adsorbing drugs on the diluents.

The emulsions are formed by mixing the above solutions with suitable aqueous diluents or diluting the solutions with the diluents. The preparations filled in capsules are formed, for example, by filling the above solutions in gelatin.

The present invention includes solid dispersions, solid dispersion pharmaceutical preparations or solubilized pharmaceutical preparations, which can rapidly disintegrate and dissolve the preparations containing the compound (I) or pharmaceutically acceptable salts thereof in the stomach.

The solid dispersions or the solid dispersion pharmaceutical preparations of the present invention drastically improve pharmacokinetic parameters such as biological availability and show the excellent oral absorbability as compared with suspensions or ordinary tablets. In addition to it, the solubilized pharmaceutical preparations of the present invention improve pharmacokinetic parameters such as biological availability and show the excellent oral absorbability as compared with suspensions or ordinary tablets.

Examples will further illustrate the solid dispersions, the solid dispersion pharmaceutical preparations and the solubilized pharmaceutical preparations of the present invention. They only explain the present invention and do not particularly limit the invention.

Meanwhile, in the following description, the compound (A) is Example 196 in WO02/16329 (Patent Literature 1).

EXAMPLE 1

A Solid Dispersion (Polyvinylpyrrolidone: 0.1-Fold Amount)

About 230 g of dichloromethane and about 57 g of methanol were added to 15 g of the compound (A) and 1.5 g of polyvinylpyrrolidone (Kolidon K30, BASF) and mixed well by shaking and dissolved. The solvent of the solution was removed by a spraydryer in the conditions of: inlet temperature of 80° C., hot air flow rate of 42 to 48 mmH$_2$0 and spray speed of 8.3 g/min. to form a solid dispersion.

EXAMPLE 2

A Solid Dispersion (Polyvinylpyrrolidone: 0.5-Fold Amount)

About 227 g of dichloromethane and about 56 g of methanol were added to 15 g of the compound (A) and 7.5 g of polyvinylpyrrolidone (Kolidon K30, BASF) and mixed well by shaking and dissolved. The solvent of the solution was removed by a spray-dryer in the conditions of: inlet temperature of 80° C., hot air flow rate of 40 to 48 $mmH_2O$ and spray speed of 7.9 g/min. to form a solid dispersion.

EXAMPLE 3

A Solid Dispersion (Polyvinylpyrrolidone: 1-Fold Amount)

About 226 g of dichloromethane and about 58 g of methanol were added to 10 g of the compound (A) and 10 g of polyvinylpyrrolidone (Kolidon K30, BASF) and mixed well by shaking and dissolved. The solvent of the solution was removed by a spray-dryer in the conditions of: inlet temperature of 80° C., hot air flow rate of 38 to 44 $mmH_2O$ and spray speed of 7.7 g/min. to form a solid dispersion.

EXAMPLE 4

A Solid Dispersion (Polyvinylpyrrolidone: 5-Fold Amount)

About 227 g of dichloromethane and about 57 g of methanol were added to 3 g of the compound (A) and 15 g of polyvinylpyrrolidone (Kolidon K30, BASF) and mixed well by shaking and dissolved. The solvent of the solution was removed by a spray-dryer in the conditions of: inlet temperature of 80° C., hot air flow rate of 38 to 46 $mmH_2O$ and spray speed of 8.2 g/min. to form a solid dispersion.

EXAMPLE 5

A Solid Dispersion (Methylcellulose: 1-Fold Amount)

About 220 g of dichloromethane and about 55 g of methanol were added to 3 g of the compound (A) and 3 g of methylcellulose (Metolose SM4, Shin-Etsu Chemical Co., Ltd.) and mixed well by shaking and dissolved. The solvent of the solution was removed by a spray-dryer in the conditions of inlet temperature of 80° C., hot air flow rate of 36 to 40 $mmH_2O$ and spray speed of 10 g/min. to form a solid dispersion.

EXAMPLE 6

A Solid Dispersion (Methylcellulose: 0.1-Fold Amount)

About 220 g of dichloromethane and about 55 g of methanol were added to 30 g of the compound (A) and 3 g of methylcellulose (Metolose SM4, Shin-Etsu Chemical Co., Ltd.) and mixed well by shaking and dissolved. The solvent of the solution was removed by a spray-dryer in the conditions of: inlet temperature of 80° C., hot air flow rate of 36 to 40 $mmH_2O$ and spray speed of 10 g/min. to form a solid dispersion.

EXAMPLE 7

A Solid Dispersion (Methylcellulose: 0.5-Fold Amount)

About 222 g of dichloromethane and about 58 g of methanol were added to 15 g of the compound (A) and 7.5 g of methylcellulose (Metolose SM4, Shin-Etsu Chemical Co., Ltd.) and mixed well by shaking and dissolved. The solvent of the solution was removed by a spray-dryer in the conditions of: inlet temperature of 80° C., hot air flow rate of 40 $mmH_2O$ and spray speed of 6 g/min. to form a solid dispersion.

EXAMPLE 8

A Solid Dispersion (Hydroxypropylmethylcellulose: 5-Fold Amount)

About 218 g of dichloromethane and about 56 g of methanol were added to 3 g of the compound (A) and 15 g of hydroxypropylmethylcellulose (MetoloseTC-5E, Shin-Etsu Chemical Co., Ltd.) and mixed well by shaking and dissolved. The solvent of the solution was removed by a spray-dryer in the conditions of: inlet temperature of 80° C., hot air flow rate of 36 to 40 $mmH_2O$ and spray speed of 9 g/min. to form a solid dispersion.

EXAMPLE 9

A Solid Dispersion (Hydroxypropylmethylcellulose Phthalate: 5-Fold Amount)

About 229 g of dichloromethane and about 57 g of methanol were added to 3 g of the compound (A) and 15 g of hydroxypropylmethylcellulose phthalate (HPMCP HP55, Shin-Etsu Chemical Co., Ltd.) and mixed well by shaking and dissolved. The solvent of the solution was removed by a spray-dryer in the conditions of: inlet temperature of 80° C., hot air flow rate of 34 to 38 $mmH_2O$ and spray speed of 8.1 g/min. to form a solid dispersion.

EXAMPLE 10

A Solid Dispersion (Polyethyleneglycol: 5-Fold Amount)

About 228 g of dichloromethane and about 57 g of methanol were added to 3 g of the compound (A) and 15 g of polyethyleneglycol 6000 (PEG6000, NOF CORPORATION) and mixed well by shaking and dissolved. The solvent of the solution was removed by a spray-dryer in the conditions of: inlet temperature of 80° C., hot air flow rate of 36 to 44 $mmH_2O$ and spray speed of 8.2 g/min. to form a solid dispersion.

EXAMPLE 11

A Solid Dispersion (Polyvinylpyrrolidone: 5-Fold Amount)

100 g of the compound (A) and 500 g of polyvinylpyrrolidone (Kolidon K30) were put in a plastic bag and shaken 200 times by hands to mix them. Then, the mixed powder was volumetrically provided at the speed of about 19 g/min. to a kneader set to barrel temperature of 80° C. and screw rotation speed of 192 rpm to obtain a solid substance. The solid substance was ground by a grinding machine to form a solid dispersion.

EXAMPLE 12

A Solid Dispersion (Methylcellulose)

80 g of dichloromethane and 120 g of methanol were added to 10 g of methylcellulose (SM-4, Shin-Etsu Chemical Co., Ltd.) and mixed well and dissolved. 0.3 g of the compound (A) was added to 26.8 g of the solution, mixed well by shaking and dissolved. 0.3 g of croscarmellose sodium (Ac-Di-Sol, Asahi Kasei Corporation) was added to the solution and mixed by shaking. The solvent thereof was removed by a rotary evaporator, and the residue was further ground by a mortar to form a solid dispersion.

EXAMPLE 13

A Solid Dispersion (Hydroxypropylmethylcellulose)

80 g of dichloromethane and 120 g of methanol were added to 10 g of hydroxypropylmethylcellulose (TC-5R, Shin-Etsu Chemical Co., Ltd.) and mixed well by shaking and dissolved. 0.3 g of the compound (A) was added to 36.7 g of the solution, mixed well by shaking and dissolved. 0.3 g of croscarmellose sodium was added to the solution and mixed by shaking. The solvent thereof was removed by a rotary evaporator, and the residue was further ground by a mortar to form a solid dispersion.

EXAMPLE 14

A Solid Dispersion Pharmaceutical Preparation (Methylcellulose; Granulation by Mixing)

205 g of methanol were put into 55 g of methylcellulose (SM4, Shin-Etsu Chemical Co., Ltd.) to moisten a whole methylcellulose. 820 g of dichloromethane was added thereto, stirred and dissolved. Then, 22 g of the compound (A) was further added thereto, stirred and dissolved. Thus prepared solution was used as a spray solution mentioned below. 150 g of partially α starch (PCS PC-10, Asahi Kasei Corporation), 40 g of croscarmellose sodium (Ac-Di-Sol, Asahi Kasei Corporation), 70 g of low-substituted hydroxypropyl cellulose (LH-11, Shin-Etsu Chemical Co., Ltd.), 100 g of crystalline cellulose (Ceolas KG-802, Asahi Kasei Corporation) and 88 g of lactose (200M, DMV) were put into the mixing tank of an agitation granulator (LFS-2, Fukae Powtec Corporation), stirred by circulating hot water of about 80° C., mixed and then dried. After that, the reaction mixture was granulated by an agitation granulator with spraying 1000 g of the above prepared spray solution under nitrogen gas stream. After the completion of spraying, the mixture was stirred and dried under reduced pressure to obtain crude granules. If necessary, the mixture was additionally dried by a fluid bed dryer. The obtained crude granules were sized by mill such as a speed mill. 0.5% magnesium stearate was added to the sized granules and tableted to obtain uncoated tablets. The obtained uncoated tablets were film coated with hydroxypropylmethylcellulose to obtain a solid dispersion pharmaceutical preparation.

EXAMPLE 15

A Solid Dispersion Pharmaceutical Preparation (Methylcellulose; Fluid Bed Granulation)

A spray solution was prepared by the same method as that of Example 14. 188 g of PCS PC-10, 50 g of Ac-Di-Sol, 63 g of LH-11, 125 g of Ceolus KG-802 and 110 g of granulated lactose (DCL-11, DMV) were put into a fluid bed granulator (FLO-1, Freund Corporation), mixed and dried. Then, 1237 g of the spray solution was sprayed to conduct the fluid bed granulation. After the completion of spraying, the mixture was dried by the fluid bed granulator to obtain granules. 0.5% magnesium stearate was added to the obtained granules and tableted to obtain uncoated tablets. The obtained uncoated tablets were film coated with hydroxypropyl-methylcellulose to obtain a solid dispersion pharmaceutical preparation.

EXAMPLE 16

A Solid Dispersion Pharmaceutical Preparation (Methylcellulose; Granulation By Spray-Drying)

3.6 kg of dichloromethane, 0.9 kg of methanol and 0.5 kg of methylcellulose (SM4, Shin-Etsu Chemical Co., Ltd.) were stirred and dissolved. 116 g of Ac-Di-Sol was added thereto and dispersed, and then 2.4 kg of dichloromethane and 0.6 kg of methanol were additionally added thereto. 200 g of the compound (A) was added thereto, dissolved and dispersed. Thus obtained solution was spray-dried by a spray-dryer (TCSD, NIPPON SHARYO, LTD.) to obtain spray-dried powder. 0.76 kg of the powder was dissolved in 5.6 kg of dichloromethane and 1.4 kg of methanol, and spray-dried by the spray-dryer to obtain spray-dried powder. 82 g of the obtained spray-dried powder, 50 g of LH-11, 316 g of granulated lactose (DCL-11, DMV) and 50 g of crystalline cellulose (Avicel PH-301, Asahi Kasei Corporation) were mixed. 2.5 g of magnesium stearate was further added thereto, and thus mixed powder was tableted and film coated with hydroxypropylmethylcellulose to obtain a solid dispersion pharmaceutical preparation.

EXAMPLE 17

A Solid Dispersion Pharmaceutical Preparation (Methylcellulose; Granulation by Mixing)

658 g of methanol was put into 175 g of methylcellulose (SM4, Shin-Etsu Chemical Co., Ltd.) to moisten a whole methylcellulose. 2635 g of dichloromethane was added thereto, stirred and dissolved. Then, 35 g of the compound (A) was further added thereto, stirred and dissolved. Thus prepared solution was used as a spray solution mentioned below. 83 g of PCS PC-10, 26 g of Ac-Di-Sol, 39 g of LH-11, 77 g of Ceolus KG-802 and 103 g of lactose 200M were put into the mixing tank of an agitation granulator (LFS-2, Fukae Powtec Corporation), stirred by circulating hot water of about 80° C., mixed and then dried. After that, the reaction mixture was granulated by an agitation granulator with spraying 1100 g of the above prepared spray solution under nitrogen gas stream. After the completion of spraying, the mixture was stirred and dried under reduced pressure to obtain crude granules. If necessary, the mixture was additionally dried by a fluid bed dryer. The obtained crude granules were sized by mill such as a speed mill. 0.5% magnesium stearate was added to the sized granules and tableted to obtain uncoated tablets. The obtained uncoated tablets were film coated with hydroxypropylmethylcellulose to obtain a solid dispersion pharmaceutical preparation.

EXAMPLE 18

A Solid Dispersion Pharmaceutical Preparation (Hydroxypropylmethylcellulose; Granulation By Mixing)

302 g of methanol was put into 116 g of hydroxypropylmethylcellulose (TC-5E, Shin-Etsu Chemical Co., Ltd.) to moisten a whole hydroxypropylmethylcellulose. 705 g of dichloromethane was added thereto, stirred and dissolved. Then, 33 g of the compound (A) was further added thereto, stirred and dissolved. Thus prepared solution was used as a spray solution mentioned below. 112 g of PCS PC-10, 30 g of Ac-Di-Sol, 38 g of LH-11, 75 g of Ceolus KG-802 and 51 g of lactose 200M were put into an agitation granulator, stirred by circulating hot water of about 80° C., mixed and then dried. After that, the reaction mixture was granulated by an agitation granulator with spraying 525 g of the above prepared spray solution under nitrogen gas stream. After the completion of spraying, the mixture was stirred and dried under reduced pressure to obtain crude granules. If necessary, the mixture was additionally dried by a fluid bed dryer. The obtained crude granules were sized by mill such as a speed mill. 0.5% magnesium stearate was added to the sized granules and tableted to obtain uncoated tablets. The obtained uncoated tablets were film coated with hydroxypropylmethylcellulose to obtain a solid dispersion pharmaceutical preparation.

EXAMPLE 19

A Solid Dispersion Pharmaceutical Preparation (Methylcellulose; Fluid Bed Granulation)

About 1139 g of methanol was put into 312.5 g of methylcellulose (SM4, Shin-Etsu Chemical Co., Ltd.) to moisten a whole methylcellulose. About 4552.1 g of dichloromethane was added thereto, stirred and dissolved. Then, 250.0 g of the compound (A) was further added thereto, stirred and dissolved. Thus prepared solution was used as a spray solution mentioned below. 56.0 g of partially α starch (PCS PC-10, Asahi Kasei Corporation), 44.8 g of croscarmellose sodium (Ac-Di-Sol, Asahi Kasei Corporation), 84.0 g of crystalline cellulose (Avicel PH102, Asahi Kasei Corporation) and 22.4 g of mannitol (Mannit P, TOWA CHEMICAL INDUSTRY CO., LTD.) were put into the container of a fluid bed granulator (FLO-1, Freund Corporation), mixed and dried at intake temperature of 90° C. Then, 3500 g of the spray solution was sprayed in the conditions of the spray air pressure of 0.15 Mpa; and spray speed of 30 g/min. to conduct the fluid bed granulation. After the completion of spraying, the mixture was dried by the fluid bed granulator to obtain granules. 0.5% magnesium stearate was added to the obtained granules and tableted to obtain uncoated tablets. The obtained uncoated tablets were film coated with hydroxypropylmethylcellulose to obtain a solid dispersion pharmaceutical preparation.

EXAMPLE 20

A Solid Dispersion Pharmaceutical Preparation (Methylcellulose; Fluid Bed Granulation)

About 825.0 g of methanol was put into 225.1 g of methylcellulose (SM4, Shin-Etsu Chemical Co., Ltd.) to moisten a whole methylcellulose. About 3300.0 g of dichloromethane was added thereto, stirred and dissolved. Then, 150.1 g of the compound (A) was further added thereto, stirred and dissolved. Thus prepared solution was used as a spray solution mentioned below. 56.0 g of PCS PC-10, 44.8 g of Ac-Di-Sol, 84.0 g of Avicel PH102 and 22.4 g of Mannit P were put into a fluid bed granulator (FLO-1, Freund Corporation), mixed and dried. Then, 4200 g of the spray solution was sprayed to conduct the fluid bed granulation. After the completion of spraying, the mixture was dried by the fluid bed granulator to obtain granules. 0.5% magnesium stearate was added to the obtained granules and tableted to obtain uncoated tablets. The obtained uncoated tablets were film coated with hydroxypropylmethylcellulose to obtain a solid dispersion pharmaceutical preparation.

EXAMPLE 21

A Solid Dispersion Pharmaceutical Preparation (Methylcellulose; Fluid Bed Granulation)

About 728.2 g of methanol was put into 198.0 g of methylcellulose (SM4, Shin-Etsu Chemical Co., Ltd.) to moisten a whole methylcellulose. About 2906.7 g of dichloromethane was added thereto, stirred and dissolved. Then, 132.0 g of the compound (A) was further added thereto, stirred and dissolved. Thus prepared solution was used as a spray solution mentioned below. 70.0 g of PCS PC-10, 44.8 g of Ac-Di-Sol, 84.0 g of Avicel PH102 and 47.3 g of granulated lactose (DCL-11, DMV) were put into a fluid bed granulator (FLO-1, Freund Corporation), mixed and dried. Then, 3733.0 g of the spray solution was sprayed to conduct the fluid bed granulation. After the completion of spraying, the mixture was dried by the fluid bed granulator to obtain granules. 0.5% magnesium stearate was added to the obtained granules and tableted to obtain uncoated tablets. The obtained uncoated tablets were film coated with hydroxypropylmethylcellulose to obtain a solid dispersion pharmaceutical preparation.

EXAMPLE 22

A Solid Dispersion Pharmaceutical Preparation (Methylcellulose; Fluid Bed Granulation)

About 550.0 g of methanol was put into 150.0 g of methylcellulose (SM4, Shin-Etsu Chemical Co., Ltd.) to moisten a whole methylcellulose. About 2200.0 g of dichloromethane was added thereto, stirred and dissolved. Then, 100.0 g of the compound (A) was further added thereto, stirred and dissolved. Thus prepared solution was used as a spray solution mentioned below. 140.0 g of PCS PC-10, 44.8 g of Ac-Di-Sol, 84.0 g of Avicel PH102 and 55.1 g of DCL-11 were put into a fluid bed granulator (FLO-1, Freund Corporation), mixed and dried. Then, the spray solution was sprayed to conduct the fluid bed granulation. After the completion of spraying, the mixture was dried by the fluid bed granulator to obtain granules. 0.5% magnesium stearate was added to the obtained granules and tableted to obtain uncoated tablets. The obtained uncoated tablets were film coated with hydroxypropylmethylcellulose to obtain a solid dispersion pharmaceutical preparation.

EXAMPLE 23

A Solid Dispersion Pharmaceutical Preparation (Methylcellulose; Fluid Bed Granulation)

About 412.5 g of methanol was put into 112.5 g of methylcellulose (SM4, Shin-Etsu Chemical Co., Ltd.) to moisten a whole methylcellulose. About 1650.0 g of dichloromethane was added thereto, stirred and dissolved. Then, 75.0 g of the compound (A) was further added thereto, stirred and dissolved. Thus prepared solution was used as a spray solution mentioned below. 140.0 g of PCS PC-10, 44.8 g of Ac-Di-Sol, 84.0 g of Avicel PH102, 57.4 g of DCL-11 and 56.0 g of low-substituted hydroxypropyl cellulose (LH11, Shin-Etsu Chemical Co., Ltd.) were put into a fluid bed granulator (FLO-1, Freund Corporation), mixed and dried. Then, 2100 g of the spray solution was sprayed to conduct the fluid bed granulation. After the completion of spraying, the mixture was dried by the fluid bed granulator to obtain granules. 0.5% magnesium stearate was added to the obtained granules and tableted to obtain uncoated tablets. The obtained uncoated tablets were film coated with hydroxypropylmethylcellulose to obtain a solid dispersion pharmaceutical preparation.

EXAMPLE 24

A Solid Dispersion Pharmaceutical Preparation (Methylcellulose; Fluid Bed Granulation)

About 555.0 g of methanol was put into 150.0 g of methylcellulose (SM4, Shin-Etsu Chemical Co., Ltd.) to moisten a whole methylcellulose. About 2220.0 g of dichloromethane was added thereto, stirred and dissolved. Then, 75.0 g of the compound (A) was further added thereto, stirred and dissolved. Thus prepared solution was used as a spray solution mentioned below. 140.0 g of PCS PC-10, 44.8 g of Ac-Di-Sol, 84.0 g of Avicel PH102, 57.4 g of DCL-11 and 56.0 g of low-substituted hydroxypropyl cellulose (LH11, Shin-Etsu Chemical Co., Ltd.) were put into a fluid bed granulator (FLO-1, Freund Corporation), mixed and dried. Then, 2100 g of the spray solution was sprayed to conduct the fluid bed granulation. After the completion of spraying, the mixture was dried by the fluid bed granulator to obtain granules. 0.5% magnesium stearate was added to the obtained granules and tableted to obtain uncoated tablets. The obtained uncoated tablets were film coated with hydroxypropylmethylcellulose to obtain a solid dispersion pharmaceutical preparation.

EXAMPLE 25

A Solubilized Pharmaceutical Preparation 2 mL of 12N hydrochloric acid was taken and diluted with propylene carbonate (Showa Denko K.K.) to 20 mL thereof. 6 mL of the solution was further taken and diluted with propylene carbonate to 10 mL thereof. 0.3003 g of the compound (A) was taken and dissolved in 1.514 g of propylene carbonate containing 0.72 mol/L of hydrochloric acid. 6.00 g of polyethyleneglycol 400 was added thereto and mixed well to prepare a solubilized pharmaceutical preparation.

EXAMPLE 26

A Solid Dispersion Pharmaceutical Preparation (Foaming Preparation)

792.0 g of methanol was put into 216.0 g of methylcellulose (SM4, Shin-Etsu Chemical Co., Ltd.) to moisten a whole methylcellulose. 3169.8 g of dichloromethane was added thereto, stirred and dissolved. Then, 144.0 g of the compound (A) was further added thereto, stirred and dissolved. Thus prepared solution was used as a spray solution mentioned below. 56.0 g of partially α starch (PCS PC-10, Asahi Kasei Corporation), 44.8 g of croscarmellose sodium (Ac-Di-Sol, Asahi Kasei Corporation), 84.0 g of crystalline cellulose (Avicel PH102, Asahi Kasei Corporation) and 22.4 g of mannitol (Mannit P, TOWA CHEMICAL INDUSTRY CO., LTD.) were put into the container of a fluid bed granulator (FLO-1, Freund Corporation), mixed and dried at intake temperature of 90° C. Then, 4230 g of the spray solution was sprayed in the conditions of the spray air pressure of 0.15 Mpa; and spray speed of 30 g/min. to conduct the fluid bed granulation. After the completion of spraying, the mixture was dried by the fluid bed granulator to obtain granules. Sodium hydrogen carbonate and L-tartaric acid were mixed in the weight ratio of 1:1 by shaking by hands. Then, 15 g of the mixture was added to 150 g of the obtained granules and mixed by a V-mixer (Mix well blender V-10, TOKUJU CORPORATION) in 30 rpm for 7 minutes. Further, 0.5% magnesium stearate was added to the obtained mixture and tableted to obtain a solid dispersion pharmaceutical preparation, which is a foaming preparation.

As comparative examples, a carmellose sodium (CMCNa) suspension and ordinary tablets are explained as follows.

COMPARATIVE EXAMPLE 1

CMCNa Suspension 2.0 g of carmellose sodium (CMCNa) powder was precisely weighed and diluted by adding water to prepare 400 mL of 0.5% CMCNa solution.

Besides the above, 0.2 g of the compound (A) was precisely weighed and blended well with the CMCNa solution in an agate mortar to prepare 100 mL of CMCNa suspension.

COMPARATIVE EXAMPLE 2

Ordinary Tablets 0.3 g of the compound (A), 2.7 g of granulated lactose (DCL-11, DMV), 1.35 g of crystalline cellulose (Avicel PH-301, Asahi Kasei Corporation), 0.15 g of croscarmelose sodium (Ac-Di-Sol, Asahi Kasei Corporation) and 0.02 g of magnesium stearate were weighed and mixed by a vortex mixer. Thus obtained powder was prepared as tablets to obtain ordinary tablets.

Next, intravenous injection solutions are explained, which were used for calculating biological availability.

REFERENTIAL EXAMPLE 1

An Intravenous Administration Solution 0.1 g of the compound (A) was precisely weighed and added to about 30 mL of polyethyleneglycol 400 (NOF Corporation), and the ultrasonic treatment was conducted thereto. Thus, the mixture was dissolved, and diluted by adding polyethyleneglycol 400 to prepare 50 mL of an intravenous administration solution.

REFERENTIAL EXAMPLE 2

An Intravenous Administration Solution 0.4 g of the compound (A) was precisely weighed and added to about 80 mL of polyethyleneglycol 400 (NOF Corporation), and the ultrasonic treatment was conducted thereto. Thus, the mixture was dissolved, and diluted by adding polyethyleneglycol 400 to prepare 100 mL of an intravenous administration solution.

The effects of the solid dispersions, solid dispersion pharmaceutical preparations and solubilized pharmaceutical preparations of the present invention are explained in test examples.

TEST EXAMPLE 1

The powders obtained in Examples 1 to 11 were evaluated on the absence or presence of crystallinity with a powder X-ray diffractometer. The followings are conditions in measurement of powder X-ray diffraction patterns.
Target: Cu full-automatic monochromator
Voltage: 45 kV
Current: 45 mV
Slit: divergence ½°
: scattering ½°
: receiving 0.15 mm
Scan Speed: 2°/min.
$2\theta$ range: 5 to 40°

Examples 1 to 11 had the same results of analysis. As one example, the results of analysis of powder X-ray diffraction in the solid dispersion of Example 1 is shown in FIG. 1. FIG. 1 clarifies that the compound (A) in the solid dispersion or pharmaceutically acceptable salts thereof do not form a crystalline structure.

TEST EXAMPLE 2

A Solid Dispersion (Methylcellulose)

The tip of a flange of a syringe for 10 mL was covered with Parafilm, and 5 mL of purified water was poured therein. 0.07 g of the solid dispersion (methylcellulose) of Example 12 was precisely weighed and poured in the flange. A plunger was inserted to a gasket part in the flange and adequately shaken. Then, the solid dispersion was forcefully administered in the stomach of a beagle dog under fasting with an oral sonde in the amount of 10 mg/body (that is, 10 mg of the compound (A) per one individual, hereinafter same as above). After the administration, inside of the sonde was rinsed with 30 mL of purified water into the stomach. The samples of the blood plasma were taken before the administration and 0.25, 0.5, 1, 2, 4, 6, 8, and 24 hours after starting the administration.

TEST EXAMPLE 3

A Solid Dispersion (Hydroxypropylmethylcellulose)

The tip of a flange of a syringe for 10 mL was covered with Parafilm, and 5 mL of purified water was poured therein. 0.1285 g of the solid dispersion (hydroxypropylmethylcellulose) of Example 13 was precisely weighed and poured in the flange. A plunger was inserted to a gasket part in the flange and adequately shaken. Then, the solid dispersion was forcefully administered in the stomach of a beagle dog under fasting with an oral sonde in the amount of 10 mg/body. After the administration, inside of the sonde was rinsed with 30 mL of purified water into the stomach. The samples of the blood plasma were taken before the administration and 0.25, 0.5, 1, 2, 4, 6, 8, and 24 hours after starting the administration.

TEST EXAMPLE 4

A Solid Dispersion Pharmaceutical Preparation

Each one tablet of the solid dispersion pharmaceutical preparations of Examples 14 to 18 was directly put in an oral cavity of a beagle dog under fasting in the amount of 10 mg/body and made the dog swallow it, and 20 mL of purified water was given to it. The samples of the blood plasma were taken before the administration and 0.25, 0.5, 1, 2, 4, 6, 8, and 24 hours after starting the administration.

TEST EXAMPLE 5

A Solubilized Pharmaceutical Preparation 0.26 g of the solubilized pharmaceutical preparation of Example 25 was precisely weighed and filled in a No. 2 hard gelatin capsule. Then, the capsule was directly put in an oral cavity of a beagle dog under fasting and made the dog swallow it (10 mg/body), and 20 mL of purified water was given to it. The samples of the blood plasma were taken before the administration and 0.25, 0.5, 1, 2, 4, 6, 8, and 24 hours after starting the administration.

TEST EXAMPLE 6

A Solid Dispersion Pharmaceutical Preparation

Each one tablet of the solid dispersion pharmaceutical preparations of Examples 19 to 24 was directly put in an oral cavity of a beagle dog under fasting in the amount of 40 mg/body and made the dog swallow it, and 30 mL of purified water was given to it. The samples of the blood plasma were taken before the administration and 0.25, 0.5, 1, 2, 4, 6, 8, and 24 hours after starting the administration.

TEST EXAMPLE 7

A Solid Dispersion Pharmaceutical Preparation (Containing Foaming Agents)

One tablet of the solid dispersion pharmaceutical preparation of Example 26 was directly put in an oral cavity of a beagle dog under fasting in the amount of 40 mg/body and made the dog swallow it, and 50 mL of purified water was given to it. The samples of the blood plasma were taken before the administration and 0.25, 0.5, 1, 2, 4, 6, 8, and 24 hours after starting the administration.

COMPARATIVE TEST EXAMPLE 1

CMCNa Suspension 5 mL of carmellose sodium (CMCNa) suspension of Comparative Example 1 was forcefully administered in the stomach of a beagle dog with an oral sonde in the amount of 10 mg/body. After the administration, inside of the sonde was rinsed with 30 mL of purified water into the stomach. The samples of the blood plasma were taken before the administration and 0.25, 0.5, 1, 2, 4, 6, 8, and 24 hours after starting the administration.

COMPARATIVE TEST EXAMPLE 2

Ordinary Tablets

One tablet of the ordinary tablet of Comparative Example 2 was directly put in an oral cavity of a beagle dog under fasting in the amount of 10 mg/body and made the dog swallow it, and 20 mL of purified water was given to it. The samples of the blood plasma were taken before the administration and 0.25, 0.5, 1, 2, 4, 6, 8, and 24 hours after starting the administration.

REFERENTIAL TEST EXAMPLE 1

An Intravenous Administration Solution

The intravenous administration solution of Referential Example 1 was administered in veins of a beagle dog under fasting in the amount of 10 mg/body. The samples of the blood plasma were taken before the administration, 2, 10, 30, 60 minutes after and 2, 4, 6, 8, 24 hours after starting the administration.

REFERENTIAL TEST EXAMPLE 2

An intravenous administration solution The intravenous administration solution of Referential Example 2 was administered in veins of a beagle dog under fasting in the amount of 40 mg/body. The samples of the blood plasma were taken before the administration, 2, 10, 30, 60 minutes after and 2, 4, 6, 8, 24 hours after starting the administration.

Tables 1, 2, 3, and 4 show each pharmacokinetic parameters (Cmax, Tmax, AUC, BA) in cases of using: (i) Examples 12 and 13 which are the solid dispersions of the present invention, Example 25 which is the solubilized pharmaceutical preparation and Comparative Examples 1 and 2; (ii) Examples 14 to 18 which are the solid dispersion pharmaceutical preparations of the present invention and Comparative Examples 1 and 2; (iii) Examples 19 to 24 which are the solid dispersion pharmaceutical preparations of the present invention; and (iv) Example 26 which is the solid dispersion pharmaceutical preparation of the present invention.

Here, Cmax indicates the maximum blood concentration of each drug; Tmax indicates the time to reach the maximum blood concentration; AUC indicates the area under the blood concentration-time curve of each drug from the start of the administration until 8 hours later; and BA indicates biological availability.

TABLE 1

| Test Sample | Cmax (ng/mL) | Tmax (hr) | $AUC_{0-8}$ (ng · hr/mL) | BA (%) |
|---|---|---|---|---|
| Exam. 12*[2] | 913 ± 323.2 | 0.5 | 1252 ± 468.2 | 36 |
| Exam. 13*[2] | 1085 ± 344.2 | 0.3 | 1386 ± 115.6 | 45 |
| Exam. 25*[2] | 411 ± 170.1 | 0.4 | 512 ± 154.7 | 17 |
| Com. Exam. 1*[1] | 25 ± 7.7 | 4.8 | 49 ± 12.5 | 2 |
| Com. Exam. 2*[2] | 25 ± 18.9 | 1.7 | 63 ± 49.5 | 2 |

*[1]: Average of 6 examples ± SE
*[2]: Average of 3 examples ± SE

TABLE 2

| Test Sample | Cmax (ng/mL) | Tmax (hr) | $AUC_{0-8}$ (ng · hr/mL) | BA (%) |
|---|---|---|---|---|
| Exam. 14*[1] | 669 ± 223.9 | 1.1 | 1538 ± 222.2 | 48 |
| Exam. 15*[1] | 1038 ± 129.2 | 0.7 | 1500 ± 134.6 | 47 |
| Exam. 16*[1] | 675 ± 149.9 | 0.7 | 1224 ± 209.0 | 38 |
| Exam. 17*[1] | 1076 ± 314.6 | 0.7 | 1447 ± 227.4 | 44 |
| Exam. 18*[1] | 673 ± 173.3 | 0.8 | 1222 ± 122.3 | 39 |
| Com Exam. 1*[1] | 25 ± 7.7 | 4.8 | 49 ± 12.5 | 2 |
| Com Exam. 2*[2] | 25 ± 18.9 | 1.7 | 63 ± 49.5 | 2 |

*[1]: Average of 6 examples ± SE
*[2]: Average of 3 examples ± SE

TABLE 3

| Test Sample | Cmax (ng/mL) | Tmax (hr) | $AUC_{0-8}$ (ng · hr/mL) | BA (%) |
|---|---|---|---|---|
| Exam. 19 | 5071 ± 2018.6 | 0.7 | 7441 ± 2786.0 | 52 |
| Exam. 20 | 4183 ± 518.5 | 0.8 | 7466 ± 661.5 | 53 |
| Exam. 21 | 2618 ± 537.2 | 0.8 | 4637 ± 862.1 | 35 |
| Exam. 22 | 2603 ± 720.6 | 0.7 | 5204 ± 1187.1 | 37 |
| Exam. 23 | 3140 ± 301.9 | 0.8 | 6016 ± 773.1 | 42 |
| Exam. 24 | 2839 ± 972.2 | 1.2 | 5361 ± 864.9 | 39 |

Average of 6 examples ± SE

TABLE 4

| Test Samples | Cmax (ng/mL) | Tmax (hr) | $AUC_{0-8}$ (ng · hr/mL) | BA (%) |
|---|---|---|---|---|
| Exam. 24 | 7143 ± 2052 | 0.5 ± 0 | 12729 ± 2012 | 79 |

Average of 3 examples ± SE

As clarified from the pharmacokinetic parameters in Tables 1, 2, 3, and 4, the solid dispersions and the solid dispersion pharmaceutical preparations of the present invention show the significantly excellent oral absorbability as compared with the CMCNa suspension of Comparative Example 1 and the ordinary tablets of Comparative Example 2.

Additionally, the solubilized pharmaceutical preparations of the present invention show the excellent oral absorbability as compared with the CMCNa suspension of Comparative Example 1 and the ordinary tablets of Comparative Example 2.

The present invention provides solid dispersions or solid dispersion pharmaceutical preparations and solubilized pharmaceutical preparations, which show high solubility and oral absorbability of the compound (I) that is a poorly-soluble drug or pharmaceutically acceptable salts thereof.

The solid dispersions or solid dispersion pharmaceutical preparations and solubilized pharmaceutical preparations of present invention have an α 4 integrin inhibiting activity, and are useful as therapeutic agents or preventive agents for inflammatory diseases in which α 4 integrin-depending adhesion process participates in the pathology, rheumatoid arthritis, inflammatory bowel diseases, systemic erythematodes, multiple sclerosis, Sjogren's syndrome, asthma, psoriasis, allergy, diabetes, cardiovascular diseases, arterial sclerosis, restenosis, tumor proliferation, tumor metastasis and transplantation rejection.

What is claimed is:

1. A solid dispersion, comprising a phenylalanine compound of formula (A) or a pharmaceutically acceptable salt thereof dispersed in amorphous state in methylcellulose wherein the weight ratio of said compound of formula (A) or pharmaceutically acceptable salt thereof to said methylcellulose is 1:0.1 to 1:100

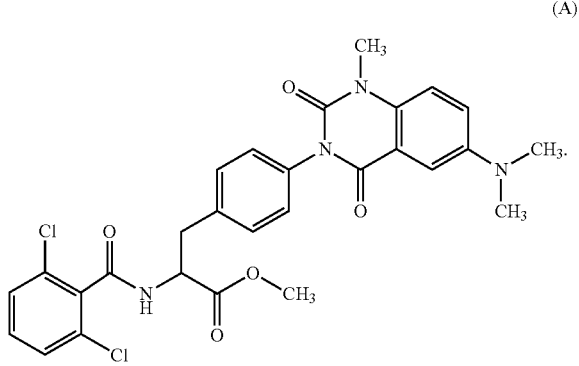 [SMILES: COC(=O)C(Cc1ccc(-n2c(=O)c3cc(N(C)C)ccc3n(C)c2=O)cc1)NC(=O)c1c(Cl)cccc1Cl]

2. The solid dispersion according to claim 1, wherein said dispersion further comprises hydroxypropylmethylcellulose.

3. The solid dispersion according to claim 1, wherein the weight ratio of said compound of formula (A) or pharmaceutically acceptable salt thereof to said methylcellulose is 1:0.25 to 1:20.

4. The solid dispersion according to claim 1, wherein the weight ratio of said compound of formula (A) or pharmaceutically acceptable salt thereof to said methycellulose is 1:05 to 1:10.

5. A solid dispersion pharmaceutical preparation which is prepared by processing a solid dispersion according to claim 1.

6. A solid dispersion pharmaceutical preparation, comprising a solid dispersion according to claim 1 and one or more foaming agents.

7. A solid dispersion pharmaceutical preparation which is prepared by coating a core component comprising a solid dispersion according to claim 1 with one or more coating agents.

8. The solid dispersion pharmaceutical preparation according to claim 7, wherein said one or more coating agents is one or more coating agents selected from the group consisting of aminoalkyl methacrylate copolymer E, hydroxypropylmethylcellulose, methylcellulose, methylhydroxyethylcellulose, opadry, carmellose calcium, carmellose sodium, polyvinylpyrrolidone, polyvinyl alcohol, dextrin, pullulan, gelatin, agar, gum Arabic, and mixtures thereof.

9. A method for producing a solid dispersion according to claim 1, comprising dissolving or dispersing the compound of formula (A) or a pharmaceutically acceptable salt thereof in one or more organic solvents together with said methylcellulose, and then removing said one or more organic solvents.

10. A method for producing a solid dispersion according to claim 1, comprising dissolving or dispersing the compound of formula (A) or a pharmaceutically acceptable salt thereof in said methylcellulose under heating, to obtain a mixture, and then cooling said mixture.

11. A method for producing a solid dispersion according to claim 1, comprising dissolving or dispersing the compound of formula (A) or a pharmaceutically acceptable salt thereof in said methylcellulose under heating and under pressure, to obtain a mixture, and then cooling said mixture.

12. A method for producing a solid dispersion according to claim 1, comprising mixing the compound of formula (A) or a pharmaceutically acceptable salt thereof together with said methylcellulose, and to obtain a mixture, then grinding the mixture.

13. The method of claim 9, wherein said one or more organic solvents is one or more organic solvents selected from the group consisting of a halogenated hydrocarbon, an alcohol, and mixtures thereof.

* * * * *